US008394944B2

(12) United States Patent
Zheng et al.

(10) Patent No.: US 8,394,944 B2
(45) Date of Patent: Mar. 12, 2013

(54) DUAL-PURPOSE PRIMERS AND PROBES FOR PROVIDING ENHANCED HYBRIDIZATION ASSAYS BY DISRUPTION OF SECONDARY STRUCTURE FORMATION

(75) Inventors: Minxue Zheng, Foster City, CA (US); John J. Quinn, Concord, CA (US); Brian D. Warner, Martinez, CA (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 2075 days.

(21) Appl. No.: 10/667,191

(22) Filed: Sep. 15, 2003

(65) Prior Publication Data

US 2004/0132061 A1 Jul. 8, 2004

Related U.S. Application Data

(60) Provisional application No. 60/412,263, filed on Sep. 20, 2002.

(51) Int. Cl.
C07H 21/04 (2006.01)
C12Q 1/68 (2006.01)
C12P 19/34 (2006.01)
(52) U.S. Cl. .................. 536/24.33; 435/6.12; 435/91.2
(58) Field of Classification Search ............... 435/6.12; 536/24.33
See application file for complete search history.

(56) References Cited

U.S. PATENT DOCUMENTS

| | | | |
|---|---|---|---|
| 5,030,557 A * | 7/1991 | Hogan et al. .................. 435/6 |
| 5,124,246 A | 6/1992 | Urdea et al. | |
| 5,200,314 A | 4/1993 | Urdea | |
| 5,256,535 A | 10/1993 | Ylikoski et al. | |
| 5,310,678 A | 5/1994 | Bingham et al. | |
| 5,525,494 A | 6/1996 | Newton | |
| 5,573,906 A * | 11/1996 | Bannwarth et al. .............. 435/6 |
| 5,622,822 A | 4/1997 | Ekeze et al. | |
| 5,624,802 A | 4/1997 | Urdea | |
| 5,648,482 A | 7/1997 | Meyer | |
| 5,710,264 A | 1/1998 | Urdea et al. | |
| 5,736,327 A | 4/1998 | Collins | |
| 5,747,248 A | 5/1998 | Collins | |
| 5,800,994 A | 9/1998 | Martinelli et al. | |
| 5,827,648 A | 10/1998 | Eastman et al. | |
| 5,849,481 A | 12/1998 | Urdea et al. | |
| 5,981,180 A | 11/1999 | Chandler et al. | |
| 6,046,807 A | 4/2000 | Chandler | |
| 6,054,568 A * | 4/2000 | Fisher ......................... 536/23.1 |
| 6,136,568 A | 10/2000 | Hiatt et al. | |
| 6,139,800 A | 10/2000 | Chandler | |
| 6,187,538 B1 | 2/2001 | Eastman et al. | |
| 6,261,773 B1 | 7/2001 | Segawa et al. | |
| 6,268,147 B1 * | 7/2001 | Beattie et al. .................. 435/6 |
| 6,268,222 B1 | 7/2001 | Chandler et al. | |
| 6,287,778 B1 | 9/2001 | Huang et al. | |
| 6,316,202 B1 | 11/2001 | Barnes et al. | |
| 6,322,980 B1 | 11/2001 | Singh | |
| 2001/0009760 A1 | 7/2001 | Horn et al. | |
| 2001/0026918 A1 | 10/2001 | Collins et al. | |
| 2002/0006643 A1 | 1/2002 | Kayyem et al. | |
| 2002/0028455 A1 * | 3/2002 | Laibinis et al. .................. 435/6 |
| 2002/0031764 A1 | 3/2002 | Koch | |

FOREIGN PATENT DOCUMENTS

| | | |
|---|---|---|
| EP | 0497784 B1 | 4/1999 |
| WO | WO 00/71243 A1 | 11/2000 |
| WO | WO 03/002762 | 1/2003 |

OTHER PUBLICATIONS

Honeyman et al. AJVR vol. 60:734-737. 1999.*
Stratagene Catalog p. 39. 1988.*
Switzer et al. Biochemistry vol. 32:10849-10496. 1993.*
Mir et al. (2000), "Sequence Variation in Genes and Genomic DNA: Methods for Large-Scale Analysis," *Annu. Rev. Genomics. Hum. Genet.* 1:329-360.
Whitcombe et al. (1999), "Detection of PCR Products Using Self-Probing Amplicons and Fluorescence," *Nature Biotechnology* 17:804-807.
Honeyman et al. (1999), "Development of a Snapback Method of Single-Strand Conformation Polymorphism Analysis for Genotyping Golden Retrievers for the X-Linked Muscular Dystrophy Allele," *AJYR* 60(6):734-737.
Lin et al. (1989), "Synthesis and Duplex Stability of Oligonucleotides Containing Cytosine-Thymine Analogues," *Nucleic Acids Research* 17(24):10373-10383.
Wilton et al. (1998), "Snapback SSCP Analysis: Engineered Conformation Changes for the Rapid Typing of Known Mutations," *Human Mutation* 11:252-258.
European Search Report for European counterpart application EP 06017482.8.

* cited by examiner

*Primary Examiner* — Prabha Chunduru

(57) ABSTRACT

The present invention provides primers and probes to be used in a method of enhancing hybridization of a probe to a target nucleotide sequence when the target sequence is capable of forming intramolecular secondary structures that interfere with hybridization of the probe to the target sequence. In particular, the invention includes a primer for amplifying a target nucleotide sequence, wherein at least a portion of the target nucleotide sequence can form an intramolecular secondary structure. The primer of the invention includes a primer nucleotide sequence complementary to a portion of the target nucleotide sequence that does not form a secondary structure, and a blocking sequence substantially complementary to at least a portion of the secondary structure-forming region of the amplified target nucleotide sequence, wherein the blocking sequence hybridizes to a portion of the secondary structure-forming region of the amplified target nucleotide sequence and blocks the formation of the secondary structure.

27 Claims, 10 Drawing Sheets

DUAL-PURPOSE PRIMERS AND PROBES FOR PROVIDING ENHANCED HYBRIDIZATION ASSAYS BY DISRUPTION OF SECONDARY STRUCTURE FORMATION

TECHNICAL FIELD

This invention relates generally to primers and probes for use in nucleic acid hybridization assays, particularly polymerase chain reaction (PCR) and other amplification assays, such as may be used in the detection and quantitation of single nucleotide polymorphisms (SNPs).

BACKGROUND

Nucleic acid hybridization is a widely used method for identifying specific sequences of nucleic acids. Hybridization is based upon pairing between complementary nucleic acid strands. Single-stranded oligonucleotides having known sequences can be used as hybridization probes to identify target sequences of nucleic acid analytes, by exposing the probes to sample solutions containing a nucleic acid analyte of interest. If a nucleic acid analyte hybridizes to a probe, the analyte necessarily contains the target sequence. Various aspects of this method have been studied in detail. In essence, all variations allow complementary base sequences to pair and form double-stranded molecules, and a number of methods are known in the art to determine whether pairing has occurred, such as those described in U.S. Pat. No. 5,622,822 to Ekeze et al. and U.S. Pat. No. 5,256,535 to Ylikoski et al.

Another method of detecting the binding of a probe to a target sequence is described by Whitcombe et al. (1999), "Detection of PCR products using self-probing amplicons and fluorescence," Nature Biotechnology 17:804-807. The method involves use of a probe containing a nucleotide sequence that is not amplified during the polymerase chain reaction (PCR), wherein the probe is designed to form a hairpin structure in which a fluorophore and a quencher are in self-quenching proximity. Upon denaturation and hybridization with a target nucleotide sequence, however, the segment of the probe that was formerly in the hairpin structure hybridizes with the amplified target sequence, and is detectable by the increased fluorescence. This "Scorpion" probe combines the functions of a PCR primer and a detection probe and provides enhanced amplification and detection, in part due to the unimolecular nature of the binding reaction of the fluorescent probe to the target nucleotide sequence, which increases the rate and extent of the reaction. This technology is also described in U.S. Pat. No. 5,525,494 to Newton. Detection of genetic variation among individuals is another application of sequence-specific hybridization technologies. Detection and analysis of allelic variations or SNPs in DNA typically involves chain extension and amplification using primers targeted for a specific sequence. The amplified DNA is then used as a target for various labeled oligonucleotide probes to identify point mutations and allelic sequence variation. If, however, the target DNA forms intra-molecular secondary structures, the DNA may not be able to hybridize with the primer or labeling probes efficiently or at all, thus resulting in no signal for the presence or absence of an SNP at the location of the secondary structure.

Such intramolecular secondary structures in a single-stranded nucleic acid, such as rRNA or denatured DNA, arise from the intramolecular formation of hydrogen bonds between complementary nucleotide sequences within the single-stranded nucleic acid itself. This residual secondary structure can sterically inhibit, or even block, hybrid formation between an oligonucleotide, for example a DNA or RNA oligomer being used as a probe, and its complementary sequence in the RNA or DNA (e.g., ribosomal RNA, mRNA, or DNA) that the probe targets.

There are numerous cases in which there is difficulty in determining the presence or absence of SNPs in a particular target nucleic acid. For example, cytochrome P450 exists in several allelic variations, which are associated with altered metabolism of drugs and/or cancer susceptibility. One variant of cytochrome P450, cytochrome P450 CYP2D6, has an SNP in each of the four exons of the P450 CYP2D6 gene. In experiments performed to test for the presence of these SNPs, difficulties have been encountered in detecting SNPs in exons 1 and 2, due to significant secondary structure in the regions of analytical interest in these exons. Although exons 1 and 2 can be amplified with conventional primer sets, the product cannot be detected in the SNP assay. Problems in probing exons 1 and 2 were eventually linked to intra-molecular secondary structure in these two amplicons. This secondary structure precludes hybridization of allele-specific discrimination probes that would be used in an assay for these SNPs. The structures of these exons are shown in FIG. 1, where it can be seen that exons 6 and 9 exhibit relatively little difficulty for PCR and hybridization with discrimination probes, whereas exons 1 and 2 show significant secondary structure in the region of the SNP. The analysis region and the SNP are shown in red in FIG. 1.

One solution to this problem of enhancing hybridization of a probe to a target nucleotide sequence when the target sequence forms intramolecular secondary structures has been proposed in U.S. Pat. No. 5,030,557 to Hogan et al. In this patent, Hogan et al. describe how the addition of a helper nucleic acid sequence in molar excess (at least about 5 times that of the probe and up to 100 or more times that of the probe) to the nucleic acid probe sequence aids in hybridization of the probe sequence to the target sequence. In fact, Hogan et al. demonstrate the effectiveness of their approach using molar ratios of helper oligonucleotide to probe oligonucleotide of 60:1, 100:1 and 250:1. In addition, Hogan et al. state that the helper oligonucleotides should be longer than about 20 to about 50 nucleotides in length in order to be effective in blocking the formation of the secondary structure.

Therefore, there is a need in the art to provide improved hybridization probes and methods of detecting sequences contained within regions of a target molecule that tend to form an unwanted secondary structure. The method described by Hogan et al. provides one such solution. This method, however, has the disadvantages of requiring a large excess of helper oligonucleotide over probe oligonucleotide, and of constraining the length of the helper oligonucleotides.

SUMMARY OF THE INVENTION

The present invention addresses the aforementioned need in the art, and in a first embodiment provides a primer that includes both a primer sequence effective to amplify a target nucleotide sequence in a target molecule, and a blocking sequence that disrupts secondary structure formation in a single-stranded form of the target molecule, or in an amplicon formed during an amplification assay (accordingly, the primer is sometimes referred to herein as a "dual-purpose" primer). A primer having these combined features is useful in a method for detecting the presence or absence of a site of interest (e.g., an SNP) contained within or proximal to the secondary structure-forming region, wherein the site of interest, in the absence of the primer, would be concealed by formation of the unwanted secondary structure. In contrast to prior methods for detecting nucleic acid sequences that are potentially "hidden" within a secondary structure, such as the methods discussed above, the present invention enables amplification using a single primer oligonucleotide, wherein the primer contains a blocking sequence that can be substantially shorter than the blocking probes of the prior art (e.g., those described by Hogan et al.) and does not have to have perfect complementarity with the region in the target molecule that forms the unwanted secondary structure.

In another embodiment, a method is provided for using the dual-purpose primer in a method amplifying a target nucleotide sequence in a target molecule, wherein the target nucleotide sequence contains a site of interest proximal to or contained within a secondary structure forming region capable of forming an unwanted secondary structure in an amplicon formed under amplification conditions, and the method comprises: contacting the target nucleotide sequence under hybridizing conditions, together or sequentially, with a dual-purpose primer of the invention that is complementary to one terminus of a first strand of the target molecule, a second primer complementary to the opposing terminus of the second strand of the target molecule, nucleotides appropriate to amplification, and an agent for polymerization of the nucleotides (e.g., a polymerase), wherein amplicons formed during the method do not contain the unwanted secondary structure, so that the site of interest is accessible to a hybridizing oligonucleotide.

A preferred such method is implemented in the context of using PCR to amplify a sequence of a double-stranded target DNA molecule having a first terminus and a second terminus, which comprises (a) heating a sample containing the double-stranded DNA to a temperature effective to denature the DNA and thereby provide a first single strand of DNA and a second strand of DNA, (b) contacting the denatured DNA with first and second oligonucleotide primers each comprised of a target binding sequence complementary to the first terminus of the first DNA strand and to the second terminus of the second DNA strand, respectively, (c) cooling the sample so as to allow hybridization of first and second oligonucleotide primers to the first and second strands of DNA, respectively, (d) replicating the DNA using a DNA polymerase, and repeating the aforementioned steps (a) through (d) to provide multiple copies of the sequence of double-stranded DNA, wherein the improvement comprises employing as the first primer a dual-purpose primer as provided herein.

In a related embodiment, the invention encompasses an amplicon formed by the action of a DNA polymerase on a dual-purpose primer of the invention following hybridization of the primer to a target nucleotide sequence in a target molecule.

In a further embodiment, kits are provided for carrying out amplification methods using a dual-purpose primer of the invention. One such kit is for determining the genotype of an individual, wherein the components of the kit include a dual-purpose primer of the invention, nucleotides appropriate to amplification of an oligonucleotide sequence, and an agent for polymerization of the nucleotides. Another kit for determining the genotype of an individual includes a dual-purpose primer of the invention, a second primer, nucleotides appropriate to DNA amplification, an agent for polymerization of the nucleotides, an allele specific hybridization (ASH) probe having a nucleotide capture region, and color-coded detecting means having a nucleotide capture region complementary to the nucleotide capture region on the ASH probe, wherein the nucleotide capture region on the detecting means is complementary to the ASH probe such that the target nucleotide sequence is identified by the color-coding of the detecting means.

In another embodiment, the invention provides a dual-purpose hybridization probe that (a) a probe nucleotide sequence complementary to a first nucleotide sequence in a target molecule, and (b) a blocking sequence that is substantially complementary to a second nucleotide sequence in a target molecule, wherein hybridization of the blocking sequence with the second nucleotide sequence prevents secondary structure formation in the second nucleotide sequence that would otherwise interfere with hybridization of the probe sequence to the first nucleotide sequence. The hybridization probe may be used in any assay format, although the probe is most useful in an assay for detecting the presence of a target nucleotide sequence in a target molecule wherein the target nucleotide sequence is proximal to or contained within a secondary structure forming region capable of forming an unwanted secondary structure that would prevent detection of the target nucleotide sequence.

BRIEF DESCRIPTION OF THE DRAWINGS

The file of this patent contains at least one drawing executed in color. Copies of this patent with color drawings will be provided by the Patent and Trademark Office upon request and payment of the necessary fee.

DETAILED DESCRIPTION OF THE INVENTION

Figure 1:
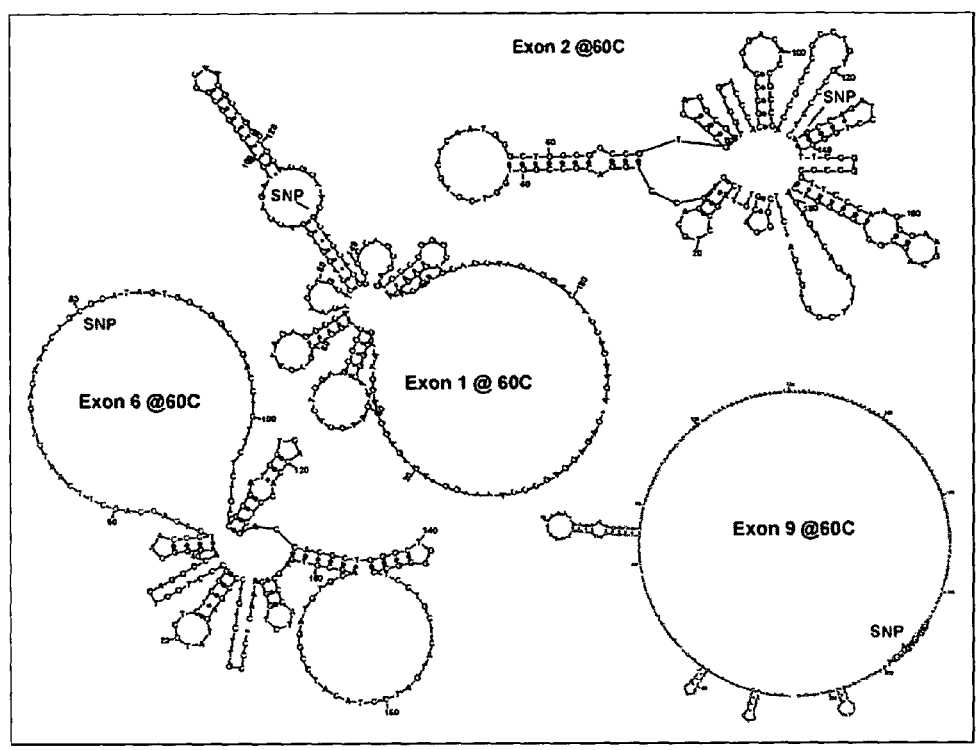
FIG. 1 schematically illustrates the structure of exons 1, 2, 6 and 9 (SEQ ID NOS: 24-27, respectively) of cytochrome P450 CYP2D6, showing the site of each SNP region in red.

Before describing the present invention in detail, it is to be understood that unless otherwise indicated this invention is not limited to specific sources of DNA, specific sequences, or specific assay formats, as such may vary. It is also to be understood that the terminology used herein is for the purpose of describing particular embodiments only, and is not intended to be limiting.

It must be noted that, as used in this specification and the appended claims, the singular forms "a," "an," and "the" include plural referents unless the context clearly dictates otherwise. Thus, for example, the term "an oligonucleotide" is intended to mean a single oligonucleotide or two or more oligonucleotides that may be the same or different, and the like.

In describing and claiming the present invention, the following terminology will be used in accordance with the definitions set out below.

It will be appreciated that, as used herein, the terms "nucleoside" and "nucleotide" refer to nucleosides and nucleotides containing not only the conventional purine and pyrimidine bases, i.e., adenine (A), thymine (T), cytosine (C), guanine (G), and uracil (U), but also modified nucleosides and nucleotides. Such modifications include, but are not limited to, methylation or acylation of a purine or pyrimidine moiety, substitution of a different heterocyclic ring structure for a pyrimidine ring or for one or both rings in the purine ring system, and protection of one or more functionalities, e.g., using a protecting group such as acetyl, difluoroacetyl, trifluoroacetyl, isobutyryl, benzoyl, and the like. Modified nucleosides and nucleotides also include modifications on the sugar moiety, e.g., wherein one or more of the hydroxyl groups are replaced with halide and/or hydrocarbyl substituents (typically aliphatic groups, in the latter case), or are functionalized as ethers, amines, or the like. Common analogs include, but are not limited to, 1-methyladenine, 2-methyladenine, $N^6$-methyladenine, $N^6$-isopentyl-adenine, 2-methylthio-$N^6$-isopentyladenine, N,N-dimethyladenine, 8-bromoadenine, 2-thiocytosine, 3-methylcytosine, 5-methylcytosine, 5-ethylcytosine, 4-acetylcytosine, 1-methylguanine, 2-methylguanine, 7-methylguanine, 2,2-dimethylguanine, 8-bromo-guanine, 8-chloroguanine, 8-aminoguanine, 8-methylguanine, 8-thioguanine, 5-fluoro-uracil, 5-bromouracil, 5-chlorouracil, 5-iodouracil, 5-ethyluracil, 5-propyluracil, 5-methoxyuracil, 5-hydroxymethyluracil, 5-(carboxyhydroxymethyl)uracil, 5-(methyl-aminomethyl)uracil, 5-(carboxymethylaminomethyl)-uracil, 2-thiouracil, 5-methyl-2-thiouracil, 5-(2-bromovinyl)uracil, uracil-5-oxyacetic acid, uracil-5-oxyacetic acid methyl ester, pseudouracil, 1-methylpseudouracil, queosine, inosine, 1-methylinosine, hypoxanthine, xanthine, 2-aminopurine, 6-hydroxyaminopurine, 6-thiopurine, and 2,6-diaminopurine. Iso-guanine and iso-cytosine may be incorporated into oligonucleotides to lower potential cross reactivity between sequences when hybridization is not desired.

As used herein, the term "oligonucleotide" encompasses polydeoxyribonucleotides (containing 2-deoxy-D-ribose), polyribonucleotides (containing D-ribose), any other type of polynucleotide that is an N-glycoside of a purine or pyrimidine base, and other polymers containing normucleotidic backbones (e.g., protein nucleic acids and synthetic sequence-specific nucleic acid polymers commercially available from the Anti-Gene Development Group, Corvallis, Oreg., as Neugene™ polymers) or nonstandard linkages, providing that the polymers contain nucleobases in a configuration that allows for base pairing and base stacking, such as is found in DNA and RNA. Thus, "oligonucleotides" herein include double- and single-stranded DNA, as well as double- and single-stranded RNA and DNA:RNA hybrids, and also include known types of modified oligonucleotides, such as, for example, oligonucleotides wherein one or more of the naturally occurring nucleotides is substituted with an analog; oligonucleotides containing internucleotide modifications such as, for example, those with uncharged linkages (e.g., methyl phosphonates, phosphotriesters, phosphoramidates, carbamates, etc.), negatively charged linkages (e.g., phosphorothioates, phosphorodithioates, etc.), and positively charged linkages (e.g., aminoalkylphosphoramidates, aminoalkylphosphotriesters), those containing pendant moieties, such as, for example, proteins (including nucleases, toxins, antibodies, signal peptides, poly-L-lysine, etc.), those with intercalators (e.g., acridine, psoralen, etc.), those containing chelators (e.g., metals, radioactive metals, boron, oxidative metals, etc.), and those containing alkylators. There is no intended distinction in length between the terms "polynucleotide" and "oligonucleotide," and these terms will be used interchangeably. These terms refer only to the primary structure of the molecule. As used herein the symbols for nucleotides and polynucleotides are according to the IUPAC-IUB Commission of Biochemical Nomenclature recommendations (*Biochemistry* 9:4022, 1970).

Oligonucleotides can be synthesized by known methods. Background references that relate generally to methods for synthesizing oligonucleotides include those related to 5'-to-3' syntheses based on the use of β-cyanoethyl phosphate protecting groups, e.g., de Napoli et al. (1984) *Gazz Chim Ital* 114:65; Rosenthal et al. (1983) *Tetrahedron Lett* 24:1691; Belagaje and Brush (1977) *Nuc Acids Res* 10:6295; in references which describe solution-phase 5'-to-3' syntheses include Hayatsu and Khorana (1957) *J Am Chem Soc* 89:3880; Gait and Sheppard (1977) *Nuc Acids Res* 4:1135; Cramer and Koster (1968) *Angew Chem Int Ed Engl* 7:473; and Blackburn et al. (1967), *J Chem Soc Part C*, at 2438. Additionally, Matteucci and Caruthers (1981) *J Am Chem Soc* 103:3185-91 described the use of phosphochloridites in the preparation of oligonucleotides. Beaucage and Caruthers (1981) *Tetrahedron Lett* 22:1859-62, and U.S. Pat. No. 4,415, 732 described the use of phosphoramidites for the preparation of oligonucleotides. Smith, *Am Biotech Lab* (ABL) 15-24 (December 1983) describes automated solid-phase oligodeoxyribonucleotide synthesis. See also the references cited therein, and Warner et al. (1984) *DNA* 3:401-11, the disclosures of which are incorporated herein by reference. T. Horn and M. S. Urdea (1986) *DNA* 5:421-25 described phosphorylation of solid-supported DNA fragments using bis(cyanoethoxy)-N,N-diisopropylaminophosphine. See also, T. Horn and M. S. Urdea (1986) *Tetrahedron Lett* 27:4705-08.

As used herein, the term "probe" refers to a structure comprised of a polynucleotide that forms a hybrid structure with a target sequence contained in a molecule (a "target molecule") in a sample undergoing analysis, due to complementarity of at least one sequence in the probe with the target sequence. The nucleotides of any particular probe may be deoxyribonucleotides, ribonucleotides, and/or synthetic nucleotide analogs. The term "primer" refers to an oligonucleotide, whether produced naturally as in a purified restriction digest or produced synthetically, which is capable of acting as a point of initiation of synthesis when placed under conditions in which synthesis of a primer extension product that is complementary to a nucleic acid strand is induced, i.e., in the presence of appropriate nucleotides and an agent for polymerization such as a DNA polymerase in an appropriate buffer and at a suitable temperature.

The term "support" refers to any solid surface (including semi-solid surfaces) to which a probe, analyte molecule, or other chemical entity may be anchored. Suitable support materials include, but are not limited to, supports that are typically used for solid phase chemical synthesis, e.g., polymeric materials (e.g., polystyrene, polyvinyl acetate, polyvinyl chloride, polyvinyl pyrrolidone, polyacrylonitrile, polyacrylamide, polymethyl methacrylate, polytetrafluoroethylene, polyethylene, polypropylene, polyvinylidene fluoride, polycarbonate, divinylbenzene styrene-based polymers), agarose (e.g., Sepharose®), dextran (e.g., Sephadex®), cellulosic polymers and other polysaccharides, silica and silica-based materials, glass (particularly controlled pore glass, or "CPG") and functionalized glasses and ceramics. Preferred supports are solid substrates in the form of beads or particles, including microparticles and nanoparticles.

By "PCR" is meant herein the polymerase chain reaction (PCR) technique, disclosed by Mullis in U.S. Pat. Nos. 4,683,195 (Mullis et al) and 4,683,202, incorporated herein by reference. In the PCR technique, short oligonucleotide primers are prepared that match opposite ends of a desired sequence. The sequence between the primers need not be known. A sample of DNA (or RNA) is extracted and denatured (preferably by heat). Then, oligonucleotide primers are added in molar excess, along with dNTPs and a polymerase (preferably Taq polymerase, which is stable to heat). The DNA is replicated, then again denatured. This results in two "long products," which begin with the respective primers, and the two original strands (per duplex DNA molecule). The reaction mixture is then returned to polymerizing conditions (e.g., by lowering the temperature, inactivating a denaturing agent, or adding more polymerase), and a second cycle initiated. The second cycle provides the two original strands, the two long products from cycle 1, two new long products (replicated from the original strands), and two "short products" replicated from the long products. The short products have the sequence of the target sequence (sense or antisense) with a primer at each end. On each additional cycle, an additional two long products are produced, and a number of short products equal to the number of long and short products remaining at the end of the previous cycle. Thus, the number of short products grows exponentially with each cycle. This amplification of a specific analyte sequence allows the detection of extremely small quantities of DNA.

The term "3SR" as used herein refers to a method of target nucleic acid amplification, and is also known as the "self-sustained sequence replication" system, as described in European Patent Publication No. 373,960 (published Jun. 20, 1990).

The term "LCR" as used herein refers to a method of target nucleic acid amplification also known as the "ligase chain reaction" as described by Barany (1991) *Proc. Nat. Acad. Sci.* 88:189-193.

The term "hybridizing conditions" is intended to mean those conditions of time, temperature, and pH, and the necessary amounts and concentrations of reactants and reagents, sufficient to allow at least a portion of complementary sequences to anneal with each other. As is well known in the art, the time, temperature, and pH conditions required to accomplish hybridization depend on the size of the oligonucleotide probe to be hybridized, the degree of complementarity between the oligonucleotide probe and the target, and the presence of other materials in the hybridization reaction admixture. The actual conditions necessary for each hybridization step are well known in the art or can be determined without undue experimentation.

Typical hybridizing conditions include the use of solutions buffered to a pH from about 7 to about 8.5 and temperatures of from about 30° C. to about 60° C., preferably from about 37° C. to about 55° C. for a time period of from about one second to about one day, preferably from about 15 minutes to about 16 hours, and most preferably from about 15 minutes to about three hours.

"Hybridization conditions" also include an effective buffer. Any buffer that is compatible, i.e., chemically inert, with respect to the probes and other components, yet still allows for hybridization between complementary base pairs, can be used. One particularly preferred buffer comprises 3×SSC, 50% formamide, 10% dextran sulfate (MW 500,000), 0.2% casein, 10 µg/mL poly A, and 100 µg/mL denatured salmon sperm DNA, wherein 1×SSC is 0.15 M sodium chloride and 0.015 M sodium citrate. Another particularly preferred buffer comprises 5×SSC, 0.1 to 0.3% sodium dodecyl sulfate, 10% dextran sulfate, 1 mM $ZnCl_2$, and 10 mM $MgCl_2$, wherein 1×SSC is as defined above. Other suitable buffers are known to those of ordinary skill in the art.

The term "target molecule" refers to a molecule that contains a nucleotidic segment, either oligomeric or polymeric, or that is entirely composed of an oligonucleotide or polynucleotide. A "target genome" as used herein refers to a polynucleotide encoding one or more proteins sought to be analyzed by the method of this invention. The target genome is generally a mammalian genome, and preferably a human genome, but can also be viral or bacterial. Target genomes include, but are not limited to, human hepatitis A virus (HAV), hepatitis B virus (HBV), hepatitis C virus (HCV), hepatitis D virus (HDV), human immunodeficiency virus (HIV), human papilloma virus (HPV), cytomegalovirus (CMV), herpes simplex virus (HSV), and bovine papilloma virus (BPV).

The term "singleplex" refers to a single assay that is not carried out simultaneously with any other assays. However, a "singleplex" assay is used to refer to individual assays that are carried out sequentially. Generally the assays are hybridization assays.

The term "multiplex" refers to multiple assays that are carried out simultaneously, in which detection and analysis steps are generally performed in parallel. As above, the assays are typically hybridization assays.

The terms "complementary" and "substantially complementary" refer to base pairing between nucleotides or nucleic acids, such as, for instance, between the two strands of a double-stranded DNA molecule or between an oligonucleotide primer and a primer binding site on a single-stranded nucleic acid to be sequenced or amplified. Complementary nucleotides are, generally, A and T (or A and U), or C and G. Two single-stranded RNA or DNA molecules are said to be "complementary" when the nucleotides of one strand, optimally aligned and compared and with appropriate nucleotide insertions or deletions, pair with at least 90% to 95%, and more preferably at least about 98 to 99.5%. Two single-stranded RNA or DNA molecules are said to be "substantially complementary" when the nucleotides of one strand, optimally aligned and compared and with appropriate nucleotide insertions or deletions, pair with at least about 80% of the nucleotides of the other strand.

The term "arresting linker" as used herein refers to a nucleotidic or non-nucleotidic linker, in a probe or primer, which is not amplified by the amplification enzyme.

The term "detectable label" as used herein refers to any atom or molecule that can be used to provide a detectable (preferably quantifiable) signal, and that can be attached to a nucleic acid or protein via a covalent bond or noncovalent interaction (e.g., through ionic or hydrogen bonding, or via immobilization, adsorption, or the like). Labels generally provide signals detectable by fluorescence, chemiluminescence, radioactivity, colorimetry, mass spectrometry, X-ray diffraction or absorption, magnetism, enzymatic activity, or the like. Suitable labels include fluorophores, chromophores, radioactive atoms (particularly $^{32}P$ and $^{125}I$), electron-dense reagents, enzymes, and ligands having specific binding partners. Enzymes are typically detected by their activity. For example, horseradish peroxidase (HRP) is usually detected by its ability to convert 3,3',5,5'-tetramethylbenzidine (TMB) to a blue pigment, quantifiable with a spectrophotometer. It should be understood that the above description is not meant to categorize the various labels into distinct classes, as a single label may be detected using two or more different methods. For example, $^{125}I$ can serve as a radioactive label and as an electron-dense reagent. HRP may serve as an enzyme or as an antigen for a monoclonal antibody (MAb). Further, one may combine various labels for a desired effect. For example, MAbs and avidin also require labels in the practice of this invention: thus, one might label a probe with biotin, and detect its presence with avidin labeled with $^{125}I$, or with an anti-biotin MAb labeled with HRP, or with an HRP molecule conjugated to avidin or streptavidin. Other permutations and possibilities will be readily apparent to those of ordinary skill in the art, and are considered as equivalents.

As used herein, the term "overlapping sequences" refers to two oligonucleotide sequences that share a partial common sequence. For example, the oligonucleotides GAATTC and AATTCC overlap in their common sequence AATTC. Because these two oligonucleotides both derive from the sequence GAATTCC, but have a starting point one nucleotide apart, the two nucleotides are said herein to overlap by one nucleotide.

As used herein, the term "discontinuous probe" refers to an oligonucleotide probe having two or more regions corresponding to two or more non-contiguous regions of a target nucleic acid. The two or more regions of the probe are covalently linked, either directly, through an intervening nucleotide sequence, or through an organic linker moiety (wherein an "organic linker moiety" refers to an essentially linear spacer organic molecule capable of being attached at its two ends to two distinct oligonucleotides.

The term "amplicon" refers to the amplification product resulting from amplification of a nucleic acid sequence using Polymerase Chain Reaction (PCR), Ligase Chain Reaction (LCR), or an alternative amplification technique.

For use in the present method, the amplicon must be labeled. In a first technique, labeled primers are used during the amplification step, thereby resulting in labeled amplicons as the labeled primers are incorporated into the amplicons. Labeled primers are available from commercial suppliers such as CPG, Inc. (Lincoln Park, N.J.), or they can be prepared via conjugating a label to an unlabeled primer. Labeling oligonucleotides such as primers can be carried out using conventional coupling procedures. Specific coupling procedures, however, will vary depending on the reactive group or groups present on the label and/or on the oligonucleotide.

For example, nick translation procedures known to those of skill in the art are available for substituting an unlabeled nucleotide with a labeled nucleotide through the use of DNase I and other enzymes, thereby providing a labeled amplicon. Another method for labeling includes the addition of a labeled deoxynucleotide terminal deoxynucleotidyl transferase (TdT, available from commercial suppliers such as PanVera Corp., Madison, Wis.), a DNA polymerase that can catalyze the addition of labeled deoxynucleotides to the 3'-end of DNA fragments.

A second technique for preparing labeled amplicons involves a separate labeling step wherein unlabeled amplicons are subsequently coupled to a label. The techniques described above with respect to labeling primers can also be used to attach labels to unlabeled amplicons.

Any type of label can be attached to the amplicon. Preferred labels include those moieties detectable by spectroscopic, photochemical, biochemical, immunochemical, or chemical means. Such labels include, without limitation, fluorescers, chemiluminescers, dyes, biotin, haptens, enzymes, enzyme substrates, enzyme cofactors, enzyme inhibitors, enzyme subunits, metal ions, electron-dense reagents, and radioactive isotopes (e.g., $^{32}P$). The label moiety can be directly or indirectly attached to the amplicon. Preferably, the label should be selected to withstand denaturing conditions if it is to be attached directly to the primer. It is preferred, although not necessary, that the label be biotin, which can be detected via binding with streptavidin coupled to a fluorescer, e.g., a streptavidin-phycoerythrin conjugate.

As used herein, the term "sample" refers to a fluid or tissue obtained from an organism (e.g., a mammalian organism such as a human) that contains the nucleic acid analyte to be characterized. Such samples are known in the art and include, without limitation: blood; plasma; serum; spinal fluid; lymph fluid; cell lysates; semen; secretions of the skin or respiratory, intestinal, or genitourinary tracts; tears; saliva; milk; and white blood cells.

The term "Single Nucleotide Polymorphism" (or "SNP") refers to a nucleic acid sequence differing in sequence by only one nucleic acid from a reference nucleic acid sequence, wherein the presence of the SNP is associated with a disease or other distinctive condition and thus serving an important diagnostic function. As illustrated in FIG. 1, a site of interest, such as an SNP, can be disposed within or near an intramolecular secondary structure and hence be unavailable for hybridization with a sequence-specific hybridization probe. In order to disrupt the secondary structure and render the "masked" sequences detectable, it is desirable to disrupt the region of the target nucleotide sequence using a blocking probe, so that the sequence of interest is not involved in an unwanted secondary structure and essentially "concealed" from a hybridization probe. U.S. Pat. No. 5,030,557 to Hogan et al. suggests that the addition of an extraneous blocking probe is effective to prevent formation of such a secondary structure and allow a sequence of interest to be detected. Extraneous blocking probes, however, must be present at a large molar excess with respect to the concentration of the target nucleotide sequence to be effective, and thus, have the disadvantage of placing constraints on the size of the blocking sequence that will be effective. By contrast, the present invention provides primers and probes that are effective to prevent formation of the unwanted secondary structure without need for a separate "blocker" molecule. The primers and probes of the invention include a combination of a blocking sequence and a hybridization sequence (i.e., a "primer sequence" in a primer, and a "target binding sequence" in a probe). The combination primers, or "dual-purpose" primers, provide at least a 100-fold increase in signal relative to the use of conventional primers, and at least a 5-fold to 7-fold increase in signal relative to a corresponding amplification process carried out with an external blocking probe as described above (see Example 1) A probe comprising a blocking sequence can be used to detect any specific site of interest, and is not limited to SNPs or allelic variants, although these are generally the preferred sites of interest within a target nucleotide sequence. While a probe comprising a blocking sequence may be used with any target nucleotide sequence, it is most useful when the target nucleotide sequence forms an intramolecular secondary structure masking the detection of the specific sequence.

To increase the sensitivity of detection of a specific target nucleotide sequence (e.g., a sequence associated with an allelic variant or an SNP), a primer has been designed that comprises a blocker sequence, wherein the blocker sequence hybridizes with a region of intramolecular secondary structure in the amplicon (corresponding to the region forming an intramolecular secondary structure in the target nucleotide sequence) so that the formation of the interfering intramolecular secondary structure is disrupted by the blocker. A specific hybridization probe, such as an allele specific hybridization probe, can then be used to detect the sequence of interest in the amplicon.

The primers and probes of the invention, and the methods of using the primers and probes, are described in greater detail below.

In this embodiment, a dual-purpose primer is provided that is used to amplify a target nucleotide sequence in a target molecule, the product of which is called an "amplicon." The target nucleotide sequence contains a site of interest proximal to or contained within a secondary structure forming region that, in the absence of the dual-purpose primer, results in an unwanted secondary structure in the amplicon that conceals the site of interest, i.e., prevents access to the site of interest by a hybridizing oligonucleotide. The site of interest is a nucleic acid sequence of two or more nucleotides, typically three or more nucleotides. Frequently, the site of interest is a three-nucleotide sequence corresponding to a possible single nucleotide polymorphism.

Figure 5:
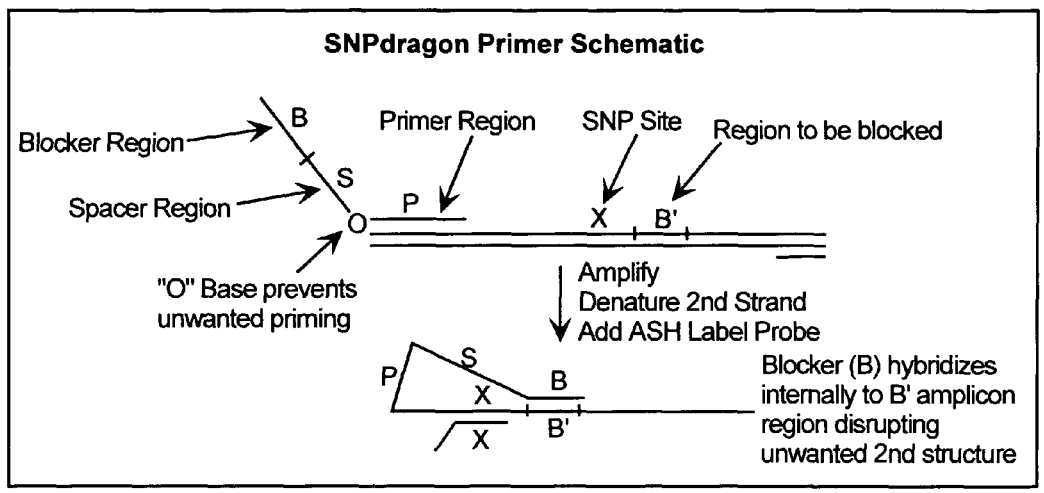
FIG. 5 schematically illustrates the structure and mechanism of action of a dual-purpose primer of the invention. The blocker sequence (referred to as the "blocker region" and "B" in the figure) and the primer sequence (referred to as the "primer region" and "P" in the figure) are linked through a spacer region "S", wherein an optional base "O" is shown between S and P. The optional base prevents undesired priming 5' to the primer sequence P. The primer sequence is complementary to one terminus of the target molecule that contains the SNP site (designated "X"), and the blocking sequence is substantially complementary to a sequence B' immediately adjacent to X, wherein B' is the segment of the target molecule responsible for generating an intramolecular secondary structure that, in the absence of the dual purpose primer, would conceal the SNP site from a complementary sequence (thereby preventing hybridization and detection). After amplification of the target nucleotide sequence and reannealing, B hybridizes with B' in the amplicon, blocking formation of the unwanted secondary structure. Detection of the SNP site is accomplished using a label probe (referred to in the figure as the "ASH Label Probe").

As illustrated in FIG. 5, the dual-purpose primer is complementary to one terminus of the target molecule containing the target nucleotide sequence. The primer contains a primer sequence (P) complementary to a segment of the target nucleotide sequence other than the secondary structure forming region (B'), and a blocking sequence (B) substantially complementary to a segment of the secondary structure-forming region to prevent formation of the unwanted secondary structure. The primer sequence is relatively short, generally on the order of 10 to 30 bases in length. The blocking sequence can also be relatively short, significantly shorter than the blocking probes used in prior methods, as discussed elsewhere herein. For example, the blocking sequence may be only about 8 to 12 bases in length.

The primer further includes an optional spacer between the primer sequence and the blocking sequence, wherein the spacer is designed not to hybridize or interfere with the hybridization events necessary for carrying out the present methods, and, as such, is referred to herein as a "nonhybridizing" spacer. The spacer may be nucleotidic, e.g., comprised of a sequence of non-natural nucleotides such as iso-guanine and iso-cytosine, or a sequence of a recurring single nucleotide. The spacer may also be non-nucleotidic, e.g., comprised of a synthetic hydrophilic oligomer such as a poly (alkylene oxide) chain. Methods suitable for preparing the optional spacer are known from the literature. The preparation of polyethylene glycol spacers is described, for example, by Kern et al. (1979) *Makromol. Chem.* 150:2539. Other spacers can be prepared in a similar manner.

In a preferred embodiment, the primer includes a means for halting transcription between the probe sequence and a nucleotidic spacer. In general, the means for halting transcription is a linker joining the two primer segments that prevents the polymerase used from continuing replication across the probe sequence—nucleotidic spacer junction. Such linkers are referred to as "arresting linkers" herein. Preferred arresting linkers comprise at least one nucleotide modified so as to act in the aforementioned manner, wherein the modification is a molecular segment extending from the molecular core of a nucleoside, typically from a nitrogen atom contained within a purine or pyrimidine ring structure. Examples of particularly preferred arresting linkers include, without limitation, $N^4$-modified pyrimidines such as 5-methyl-$N^4$—(O-6-oxyhexyl)-2'-deoxyctyidine, 5-methyl-$N^4$—(O-FMOC-6-oxyhexyl)-2'-deoxyctyidine, 5-methyl-$N^4$—(O-levulinyl-6-oxyhexyl)-2'-deoxycytidine, and 5-methyl-$N^4$—(O-6-oxyhexyl)-2'-thymidine, which are generally, although not necessarily, introduced during primer synthesis using the corresponding 3'- and 5'-substituted nucleoside, e.g., a nucleoside substituted at the 3' position with DMT and at the 5' position with a phosphoramidite. Other information regarding suitable arresting linkers, including detailed procedures for incorporation into a primer oligonucleotide, may be found in U.S. Pat. No. 5,200,314 to Urdea.

The primer can include a detectable label, although a label may also be introduced, e.g., via a label probe, during the amplification assay. In the former case, the labeled primer will result in a labeled amplicon, as the labeled primers are incorporated into the amplicons. Labeled primers are available from commercial suppliers such as CPG, Inc. (Lincoln Park, N.J.), or they can be prepared via conjugating a label to an unlabeled primer. Labeling oligonucleotides such as primers can be carried out using conventional coupling procedures. Specific coupling procedures, however, will vary depending on the reactive group or groups present on the label and/or on the oligonucleotide. Preferred labels include those moieties detectable by spectroscopic, photochemical, biochemical, immunochemical, or chemical means. Such labels include, without limitation, fluorescers, chemiluminescers, dyes, biotin, haptens, enzymes, enzyme substrates, enzyme cofactors, enzyme inhibitors, enzyme subunits, metal ions, electron-dense reagents, and radioactive isotopes (e.g., $^{32}P$). The label moiety can be directly or indirectly attached to the primer. Preferably, the label should be selected to withstand denaturing conditions if it is to be attached directly to the primer. It is preferred, although not necessary, that the label be biotin, which can be detected via binding with streptavidin coupled to a fluorescer, e.g., a streptavidin-phycoerythrin conjugate.

As indicated above, the dual-purpose primer is useful in a method for amplifying a target nucleotide sequence in a target molecule, wherein the target nucleotide sequence contains a site of interest proximal to or contained within a secondary structure forming region capable of forming an unwanted secondary structure in an amplicon formed under amplification conditions. Amplification may be carried out using conventional techniques, and although any known amplification method can be used, preferred methods include PCR, 3SR, and LCR, with PCR being most preferred.

PCR amplification using the dual-purpose primers of the invention is carried out in a mixture comprising the target molecule, a dual-purpose primer complementary to one terminus of one strand of a double-stranded target molecule, a second oligonucleotide primer complementary to the opposing terminus of the second strand of the target molecule, an excess of the four oligonucleotide (dNTP) monomers, and water that contains a buffer suitable for carrying out PCR (including conventional buffers comprising Tris-HCl, KCl, and $MgCl_2$), and an agent for polymerization of the nucleotides, e.g., a polymerase such as Taq polymerase. The mixture is then exposed to a series of replication cycles based on temperature. For example, the mixture is heated to about 94-96° C. for several minutes during which time any double-stranded DNA is denatured into single-stranded DNA. Next, the temperature of the mixture is lowered to about 50-65° C., during which time the oligonucleotide primers hybridize via hydrogen bonds to complementary sequences. Finally, the temperature of the mixture is increased to about 72° C., during which time the polymerase binds and extends a complementary strand from each primer. Since the sequence being amplified doubles after each sample, a theoretical amplification of one billion can be attained, thereby providing ample nucleic acid analyte for the present method.

Figure 2:
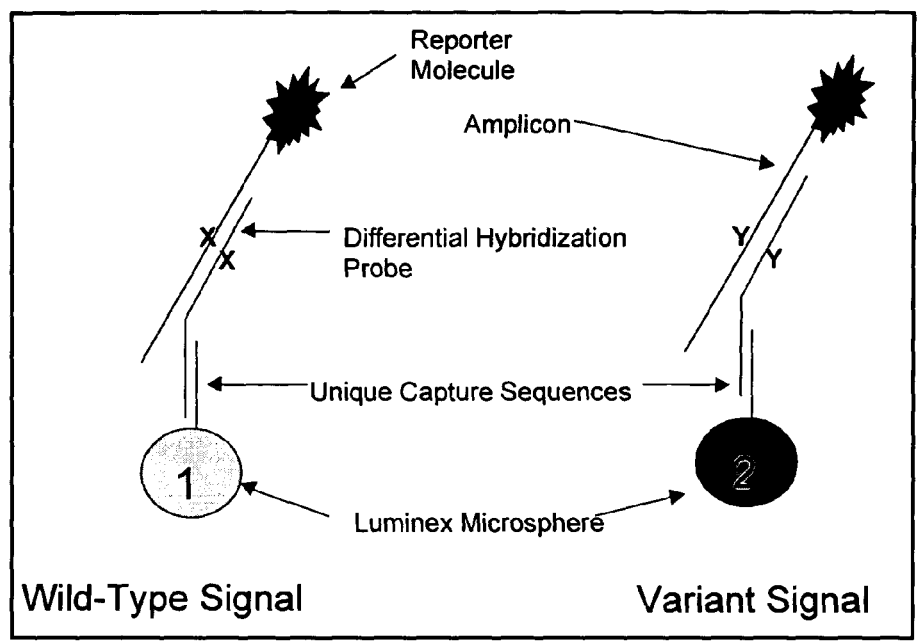
FIG. 2 schematically illustrates an overall schematic of the primers and probes used to detect an SNP in multiplex mode, and detection using Luminex™ microspheres.
Figure 3:
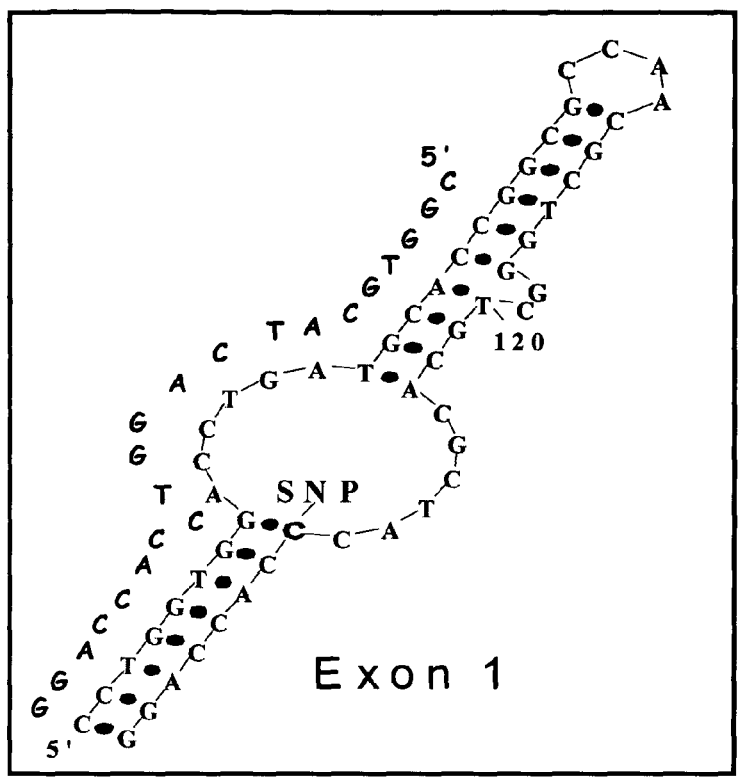
FIG. 3 schematically illustrates the interfering secondary structure containing the SNP in exon 1 (residues 142-195 of SEQ ID NO: 24) of cytochrome P450 CYP2D6, showing that the SNP is involved in a single-stranded hairpin (with the SNP region shown in red). A blocking oligonucleotide (SEQ ID NO: 28) will hybridize with the nucleotides involved in the potential intramolecular secondary structure to inhibit the formation thereof and thus allowing detection of the SNP.

A method of using the primer for amplification of a target nucleotide sequence is illustrated in FIG. 2. The blocking sequence provided in the amplicon disrupts the formation of the unwanted secondary structure in the amplicon, and therefore facilitates probing the site of interest (now in the amplicon) using the probe referred to in FIG. 2 as the "Differential Hybridization Probe" (see also FIG. 5). When the site of interest contains an allelic variation or an SNP site, the primer will amplify the region of the target nucleotide sequence containing the allelic variation or SNP site and then the allelic variation or SNP site can be detected using a differential hybridization probe comprising a detectable label or the like. Thus, the primers and methods of the invention are also useful in a method of determining the genotype of an individual. A particularly preferred method is described in U.S. patent application Ser. No. 10/666,744 to Quinn et al. for "Method for Detection of Multiple Nucleic Acid Sequence Variations," filed on even date herewith.

In the amplification of the target nucleotide sequence, mediated by the primer and a polymerization agent, e.g., a DNA polymerase or other enzyme capable of generating a complement to the target nucleotide sequence, the amplicons are detectable by the presence of a detectable label as described above, and the primers are used to amplify target nucleotide sequences derived from genomic DNA of an individual to be tested, which can be used in a method of determining the genotype of an individual.

For detection of a specific target nucleotide sequence, the invention allele specific probes are used for detecting an SNP or other sequence of interest within the amplified product generated using the primer with the target nucleotide sequence as a template, as alluded to above. The invention also facilitates the detection and analysis of an SNP or other target nucleotide sequence in a multiplexing mode, that is, in parallel hybridization experiments performed simultaneously, wherein the allele specific hybridization probes are each labeled with a unique label, as illustrated in FIG. 2. In a preferred embodiment, the unique label attached to each allele specific hybridization probe is a microsphere, which can advantageously be detected and analyzed using a flow cytometer.

Optimally, a flow cytometer linked with one or more detecting means is used for detecting the complexes, although other means for detecting and counting the captured complexes can also be used, depending on the type of label and signal. The complexes in the hybridization solution are passed through the flow cytometer, thereby allowing the detection of each complex. Preferably, the flow cytometer is linked with a first detecting means for detecting the label (of the labeled amplicon) as well as a second detecting means for detecting the signal associated with the solid substrate. Suitable equipment and methods for detecting the labels and signals using flow cytometry, and having the ability to perform multiplexing analysis, are described in U.S. Pat. Nos. 5,981,180 to Chandler et al., and 6,046,807 and 6,139,800 to Chandler. Commercially available systems are also available from Luminex Corp. (Austin, Tex.) and include, for example, the Luminex™ 100 machine. In a most preferred embodiment, the microspheres are Luminex™ microspheres. However, for purposes of determining the genotype of an individual for a single allelic variation, two unique labels are sufficient to differentiate between the binding of the allele specific hybridization probe to the wild type allele compared with the binding of the allele specific hybridization probe to the variant allele.

It will be appreciated that the probe and primer sequences need not have perfect complementarity to hybridize with the target nucleotide or amplicon thereof under hybridizing conditions. In using the probe of the invention as a hybridization probe to detect a specific sequence that may be present in a target nucleotide sequence, it is desirable that the stability of the hybridization of the blocking sequence with the target nucleotide sequence be approximately the same as the stability of the hybridization of the sequence-specific portion of the probe with the target nucleotide sequence. In this embodiment, the blocking sequence hybridizes with the secondary structure forming region of the target nucleotide sequence and blocks the secondary structure that interferes with hybridization of the sequence-specific portion of the probe, without providing a false positive result for hybridization of the sequence-specific portion of the probe. In practice, two probes are prepared that are designed to discriminate between two similar target nucleotide sequences, such as a wild type and mutant allele that it is desired to detect. The probes further comprise a unique identifying label and a sequence-specific portion designed to hybridize specifically with the sequence of the target nucleotide sequence that it is desired to detect.

Alternatively, the secondary structure blocking sequence of the probe can hybridize more strongly with the target nucleotide sequence than the sequence-specific portion of the probe. To avoid the appearance of a false positive result, the sequence-specific portion of the hybridization probe must indicate or signal that it is hybridized with the target nucleotide sequence. The presence of a label such as a fluorescent probe in which the fluorescence is either enhanced or quenched by the presence of a duplex nucleotide would accomplish this result. Another useful signal would be a self-quenched fluorophore-quencher pair in the sequence-specific portion of the probe, wherein, upon binding to the target nucleotide sequence, the sequence containing the fluorophore-quencher pair assumes a linear configuration in which the fluorescence is no longer quenched.

In addition to the primers described above, the invention also provides novel "dual-purpose" hybridization probes. The probes include: 1) a first probe nucleotide sequence complementary to a first target nucleotide sequence, and 2) a second probe sequence substantially complementary to a second target nucleotide sequence, wherein hybridization of the second probe sequence with the second target nucleotide sequence blocks secondary structure formation in the target nucleotide sequence that would otherwise interfere with binding of the first probe sequence to the first nucleotide sequence. The dual-purpose probes can be used in conjunction with any hybridization assay known in the art. The dual-purpose probes are particularly useful when the target nucleotide sequence, whether RNA or DNA, forms unwanted secondary structures as described above, wherein the secondary structures effectively mask the site of interest contained within the target nucleotide sequence. The second (blocking) sequence of the probe disrupts formation of the secondary structure in the target nucleotide sequence and facilitates probing the site of interest with the first probe nucleotide sequence. The probe is particularly useful when the sequence of interest contains an allelic variation or SNP site, which would not otherwise be detectable, and thus provides an improved method of determining the genotype of an individual.

Figure 10:
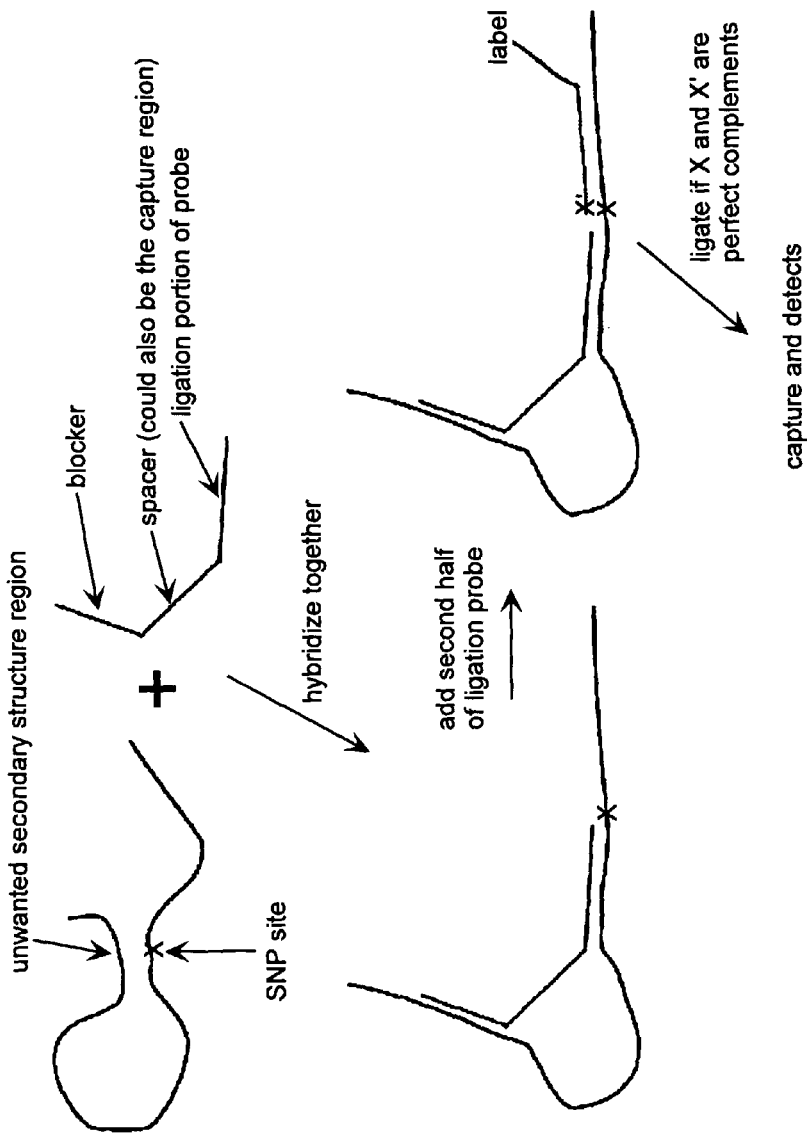
FIG. 10 schematically illustrates a dual-purpose probe that prevents formation of an unwanted secondary structure and also enables ligation detection of SNPs.

The novel probe of the present invention can be used for the dual purpose of secondary structure disruption coupled with ligation detection. Ligation assays are discussed in commonly owned U.S. Pat. No. 5,800,994 to Martinelli et al., incorporated herein by reference. A schematic representation of this procedure is set forth in FIG. 10.

A detectable label can be present on the dual-purpose hybridization probes, or attached thereto at the completion of a hybridization assay.

The invention also includes probes specific for a portion of the sequence of a target nucleotide sequence. Preferred probes are sequence-specific for a particular allele or SNP and can be used to detect a particular genotype in an individual. An allele specific hybridization (ASH) probe is an example of a preferred probe. When a target nucleotide sequence is amplified using a dual-purpose primer of the invention, the blocking sequence of the primer hybridizes with the secondary structure-forming region of the amplified target nucleotide sequence containing the particular allele or SNP. Because the blocking sequence hybridizes with the target nucleotide sequence, the ASH probe is able to hybridize with the region of the target nucleotide sequence that contains the allele or SNP, thus enabling detection of the allele or SNP.

The novel probes can further comprise a capture sequence domain designed to hybridize with a detectable probe. Preferred ASH probes comprise a sequence that hybridizes with a capture sequence domain that hybridizes with unique sequences attached to a detection means, described in greater detail below.

Detection of hybridized probes of the invention can be carried out using any method known in the art. For example, the presence of a fluorescent probe, or the lack of fluorescent signal, as in fluorescence quenching, can be used. In another method of detection, a probe can be labeled with a radioactive label and detected with a scintillant, for example. In a preferred method, a probe can be attached to a fluorophore or other dye, or the probe can be attached to a solid substrate labeled with a fluorophore or other dye. In a preferred method, the probes contain a nucleotide sequence that is complementary to a nucleotide sequence labeled with a detectable label, for example, a nucleic acid probe labeled with a fluorophore. In an especially preferred method, detection is accomplished in a multiplex assay using Luminex™ microspheres.

It may be desired to amplify the signal generated by the labeled probes. The signal amplification may involve the use of nucleic acid multimers, as described in commonly owned U.S. Pat. Nos. 5,200,314; 5,124,246; 5,624,802; 5,710,264; and 5,849,481, which describe the preparation of large comb-type branched polynucleotide multimers for use in the above-described solution phase assay. The combs provide greater signal enhancement in the assays than do the smaller multimers. Nucleic acid multimers are branched polynucleotides that are constructed to have a segment that hybridizes specifically to the analyte nucleic acid or to a nucleic acid (branched or linear) that is bound to the analyte, and iterations of a second segment that hybridize specifically to the labeled probe. In the assay employing the multimer, the initial steps are followed of hybridizing the analyte to label or amplifier probe sets, capturing probe sets in a first vessel, and transferring the complex to another vessel containing immobilized nucleic acid that will hybridize to a segment of the capturing probes. The multimer is then hybridized to the immobilized complex, and the labeled probes are in turn hybridized to the second segment iterations on the multimer. Since the multimers provide a large number of sites for label probe attachment, the signal is amplified.

The probes of the invention can be used with unamplified target nucleotide sequences if the sensitivity of detection is sufficiently high. For example, by using the multimers discussed above to detect probe bound to a target nucleotide sequence, as described in U.S. Pat. No. 5,624,802, the sensitivity can be sufficient to detect a few copies of the target sequence.

In a most preferred embodiment, detection of hybridized allele specific hybridization probes is accomplished using detectable particles that are covalently attached to the allele specific hybridization probe, wherein the particles may be microparticles, microspheres, nanoparticles, particle-functionalized beads, etc. Further ease of use is obtained by using allele specific hybridization probes comprising a unique capture sequence, which then hybridize with complementary sequences covalently attached to the microspheres or microparticles.

Suitable detectable microparticles include, without limitation, those described in U.S. Pat. No. 6,268,222, which describes particles having a diameter of less than one millimeter, preferably of a size ranging from about 0.1 to 1,000 μm in diameter, preferably 1-100 μm, more preferably 2-50 μm, even more preferably 3-25 μm, and most preferably about 6-12 μm. Microparticles are preferably made of a polymeric material such as polystyrene. However, useful polymeric materials include but are not limited to brominated polystyrene, polyacrylic acid, polyacrylonitrile, polyamide, polyacrylamide, polyacrolein, polybutadiene, polycaprolactone, polycarbonate, polyester, polyethylene, polyethylene terephthalate, polydimethylsiloxane, polyisoprene, polyurethane, polyvinylacetate, polyvinylchloride, polyvinylpyridine, polyvinylbenzylchloride, polyvinyltoluene, polyvinylidene chloride, polydivinylbenzene, polymethylmethacrylate, polylactide, polyglycolide, poly(lactide-co-glycolide), polyanhydride, polyorthoester, polyphosphazene, polyphosophaze, polysulfone, or combinations thereof. Other polymer materials (such as carbohydrate, e.g., carboxymethyl cellulose, hydroxyethyl cellulose, proteinaceous polymer, polypeptide), as well as agar, gel, eukaryotic and prokaryotic cells, viruses, lipid, metal, resin, latex, rubber, silicone (e.g., polydimethyldiphenyl siloxane), glass, ceramic, charcoal, kaolinite, bentonite, and the like, can be equally used. These polymers may also incorporate magnetic or magnetically responsive metal oxide selected from the group consisting of superparamagnetic, paramagnetic, ferromagnetic, antiferromagnetic, or ferromagnetic metal oxide.

The microparticles further comprise fluorescent or colored dyes to facilitate detection. Preferably such dyes are hydrophobic and are able to stain the microparticles. Preferred dyes are cyanine dyes. The dyes can be covalently attached to the microparticles or adsorbed. In addition, a mixture of dyes can be used to create a unique label for a particular application or for a particular probe sequence.

Also as described in U.S. Pat. No. 6,268,222, a microparticle can carry on its surface one or more populations of fluorescently stained nanoparticles, wherein all nanoparticles in a given population are dyed with the same concentration of a dye. The attachment of a known quantity of these nanoparticles, of the same or different color to the microparticle, results in a multicolored or multifluorescent microsphere. By varying the quantity and ratio of different populations of nanoparticles, it is possible to establish and distinguish a large number of discreet populations of carrier particles with unique emission spectra. The carrier microparticles can be stained as well to provide an additional color or signal. Such uniquely labeled microparticles are particularly useful for multiplex analysis of sequences, and can be conveniently detected and analyzed using flow cytometry. Of course, the use of combinations of dyes attached to nucleotide sequences or solid substrates other than microparticles or microspheres would work in a similar way and would not require the use of microparticles.

The primers and probes of the invention can also be detected using mass spectrometry to detect sequences labeled with mass tags. For example, unique capture sequences can be used that hybridize with specific sequences covalently attached to the mass tags. The presence of the mass tags would then indicate the presence of the specific capture sequence and hence the primer or allele specific hybridization probe containing the particular capture sequence. Mass tags are described and reviewed by Mir and Southern (2000), "Sequence Variation in Genes and Genomic DNA: Methods for Large-Scale Analysis," *Ann. Rev. Genomics Hum. Genet.* 1:329-360.

The practice of the present invention will employ, unless otherwise indicated, conventional techniques of molecular biology, microbiology, recombinant DNA, and immunology, which are within the skill of the art. Such techniques are explained fully in the literature. See e.g., Sambrook et al., *Molecular Cloning; a Laboratory Manual*, Third Edition (2001); *DNA Cloning*, volumes I and II (D. N Glover ed., 1985); *Oligonucleotide Synthesis* (M. J. Gait ed., 1984); *Nucleic Acid Hybridization* (B. D. Hames & S. J. Higgins eds., 1984); *Transcription And Translation* (B. D. Hames & S. J. Higgins eds., 1984); *Animal Cell Culture* (R. I. Freshney ed., 1986); *Immobilized Cells and Enzymes* (IRL Press 1986); B. Perbal, *A Practical Guide to Molecular Cloning; the series, Methods in Enzymology* (Academic Press 1984); *Gene Transfer Vectors for Mammalian Cells* (J. H. Miller and M. P. Calos Eds., Cold Spring Harbor Laboratory 1987); *Methods in Enzymology, volumes* 154 and 155 (Wu and Grossman, and Wu eds., respectively, Academic Press); *Immunochemical Methods in Cell and Molecular Biology* (Academic Press, London); Scopes (Mayer and Walker, eds. 1987), *Protein Purification: Principles and Practice*, Second Edition (Springer-Verlag, N.Y.); and *Handbook of Experimental Immunology*, volumes I-IV (D. M. Weir and C. C. Blackwell eds., 1986).

It is to be understood that while the invention has been described in conjunction with the preferred specific embodiments thereof, that the description above as well as the examples that follow are intended to illustrate and not limit the scope of the invention. Other aspects, advantages and modifications within the scope of the invention will be apparent to those skilled in the art to which the invention pertains.

All patents, patent applications, and publications mentioned herein, both supra and infra, are hereby incorporated by reference.

EXPERIMENTAL PROCEDURES

The following experimental procedures are set forth to provide those of ordinary skill in the art with a complete disclosure and description of how to make and use the hybridization probes and primers disclosed and claimed herein, and how to perform the methods using same; the examples are not intended to limit the scope of what the inventors regard as their invention. Efforts have been made to ensure accuracy with respect to numbers (e.g., amounts, temperature, etc.) but some errors and deviations should be accounted for. Unless indicated otherwise, parts are parts by weight, temperature is in degrees Celsius (° C.), and pressure is at or near atmospheric pressure at sea level.

In the procedures set forth below and throughout this specification, the abbreviations employed have their generally accepted meanings, as follows:

| | |
|---|---|
| C. | Celsius (or Centigrade) |
| mM | millimolar |
| μM | micromolar |
| pmol | picomole ($10^{-12}$ mole) |
| mg | milligram |
| μg | microgram |
| mL | milliliter |
| μL | microliter |
| μm | micrometer |
| Tm | melting temperature |
| U | units |

To carryout the procedures set forth below, a variety of software was used for primer design and Tm prediction, including Primer3, GCG®, VNTI, Primer Express®, and Hybsimulator. Hybsimulator was found to be the preferred software for Tm prediction.

Example 1

Comparison of Dual-Purpose Primer System with and without an Independent Blocking Probe The following procedures were carried out in order to compare the dual-purpose primer system with and without an independent blocker.

Extraction of Genomic DNA:

Human genomic DNA was extracted from 200 μL of EDTA-treated whole blood using QIAamp® DNA Blood Mini Kit as described by the manufacturer (Qiagen).

Preparation of Conventional Primer Sequences:

Primer sequences were designed to amplify the specific regions of DNA corresponding to the cytochrome P450 CYP2D6 gene, exons 1, 2, 6, and 9 containing the four SNP sites of interest. The biotinylated sequences also operate as the allele specific hybridization probes for the four SNP sites.

| Primer | Primer Sequence | Sequence ID No. | Primer Length |
|---|---|---|---|
| Exon 1 forward: | biotin-tagtggccatcttcctgctc | (SEQ ID NO: 1) | 20 |
| reverse: | tctggtaggggagcctcag | (SEQ ID NO: 2) | 19 |
| Exon 2 forward: | biotin-cttcggggacgtgttcag | (SEQ ID NO: 3) | 18 |
| reverse: | tcccacggaaatctgtctct | (SEQ ID NO: 4) | 20 |
| Exon 6 forward: | biotin-cccgttctgtcccgagtat | (SEQ ID NO: 5) | 19 |
| reverse: | gtttcccagatgggctcac | (SEQ ID NO: 6) | 19 |
| Exon 9 forward: | biotin-ccatggtgtctttgctttcc | (SEQ ID NO: 7) | 20 |
| reverse: | gtggggtaagcaggaatgag | (SEQ ID NO: 8) | 20 |

Preparation of Singleplex or Multiplex PCR Products:

Singleplex or multiplex reactions were carried out using 2 µL (50-70 ng) isolated genomic DNA. Twenty-five microliter reaction volumes contained 1× Titanium Taq PCR buffer, 2.5 mM each dNTPs (dATP, dCTP, dGTP, and dTTP); 0.2 µM each forward (biotinylated) and reverse primers, and 2.5 U Titanium Taq DNA polymerase. A PE 9600 thermocycler was used. The thermal cycling conditions were 94° C. for 2 min followed by 30 cycles of 95° C. for 30 sec, 68° C. for 1 minute, followed by a final extension of 5 min at 68° C.

Preparation of Multiplex Working Reagent:

The multiplex working reagent was prepared by mixing 0.1 pmol each allele specific hybridization (ASH) probe for the four SNP regions and 2000 each individual Luminex™ microspheres per 25 µL of 50 mM Hepes (containing 500 mM LiCl, 1% LDS, 1% bovine serum albumin, 10 mM $MgCl_2$, 0.01 mM $ZnCl_2$, 0.5% sodium azide, and Proclin-300 as a preservative (HIV 3.0 Label Diluent, Bayer Diagnostics), having a final pH of 7.5).

The Multiplex PCR Assay:

After completion of the PCR reaction as set forth above, 25 µL of multiplex working reagent (having the ASH probes) was added to the individual wells containing the multiplex PCR products. The plate was sealed with Mylar and the incubation was continued in the PE 9600 thermocycler. The PCR plate with the multiplex working reagent was incubated for 10 minutes at 95° C. to dissociate double-stranded DNA, followed by a 30-minute incubation at 50° C. to achieve allele specific hybridization. The plate was removed and 100 µL of wash buffer was added to each well (HIV 3.0 Wash A, Bayer Diagnostics). The contents of the wells were transferred to a 96 well pre-wetted filter plate (Multiscreen®-BV 1.2 µm, Millipore, Bedford Mass.). The wash buffer was pulled through with gentle vacuum and a 200 µL wash was repeated. The microspheres were resuspended in a 50 µL streptavidin-phycoerythrin, (0.05 µg/50 µL) TTL buffer (50 mM Tris, 400 mM LiCl, 0.1% Tween-20, pH 8.0) mixture. The plate was then wrapped in aluminum foil and incubated for 15 minutes at 25° C. with mild shaking (Titer Plate shaker, Labline Instruments). The previous wash step was repeated and the microspheres were resuspended in 80 µL of TTL buffer and read on the Luminex™ 100 in which the presence of phycoerythrin (and hence the original forward primer) and the microsphere specific for each particular ASH was detected.

Figure 4:
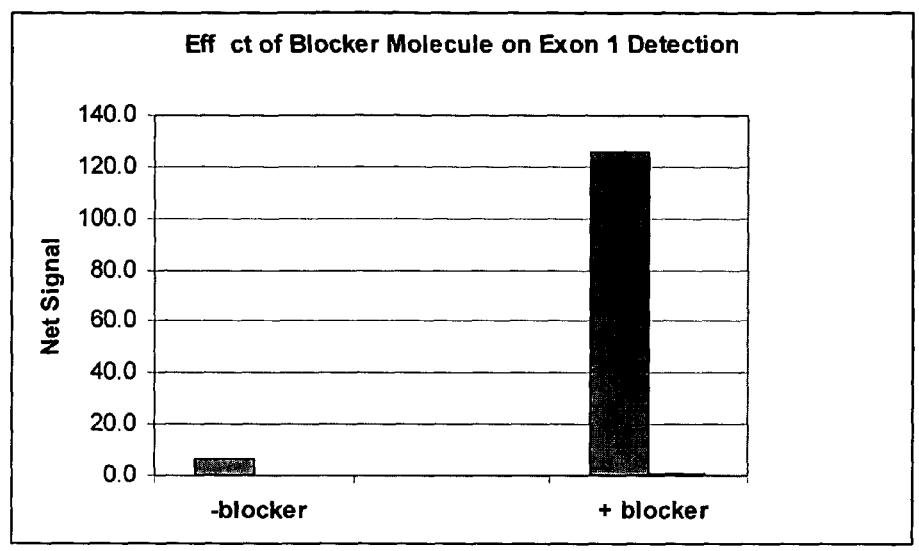
FIG. 4 is a graph showing the detection signal for the SNP in exon 1 of cytochrome P450 CYP2D6 when the blocking sequence is present, and the corresponding detection signal when the blocking sequence is absent.

Determination of Effectiveness of Independent Blocker Molecule:

To determine the effectiveness of the independent blocker molecule on the conventional PCR products set forth above, 1 pmol/25 µL blocker in the multiplex working reagent was added to the conventional cytochrome P450 CYP2D6 exon 1 PCR product. As shown in FIG. 4, the addition of the blocker molecule to the multiplex working reagent increased the signal 30 fold over the signal generated when no blocker was added to the multiplex working reagent.

Figure 6:
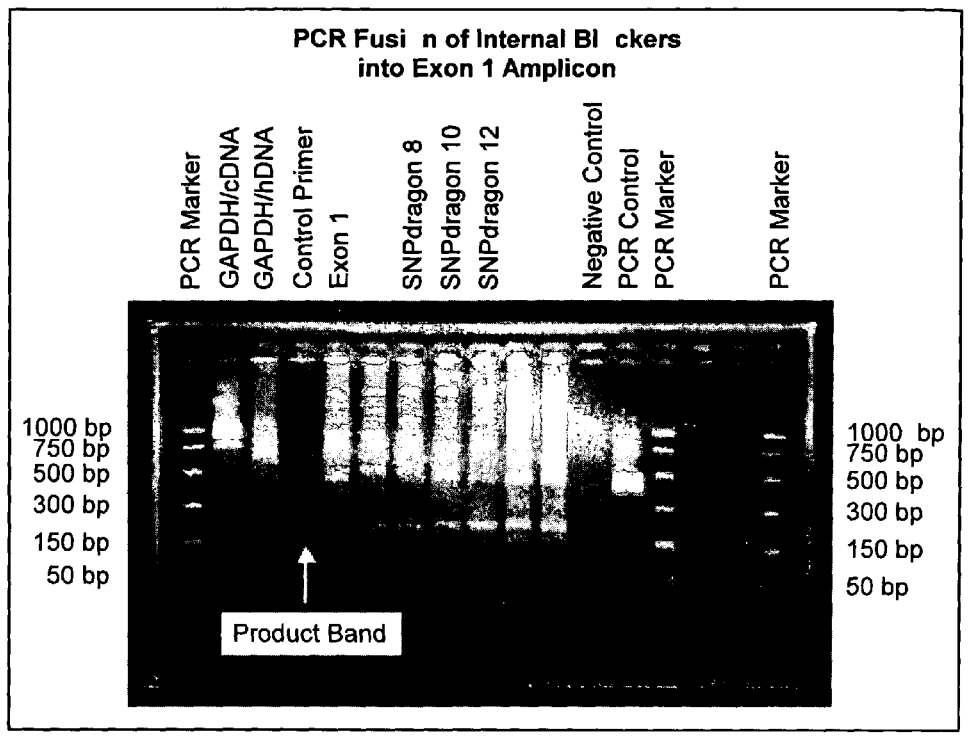
FIG. 6 shows an analytical gel demonstrating that the dual-purpose primers with blocker sequence inserts of 8, 10, and 12 nucleotides all generate a major band of expected size.

Preparation of Dual-Purpose Primer Sequences:

As seen in FIG. 1, exon 1 of the cytochrome P450 CYP2D6 gene has the greatest amount of secondary structure at the SNP. The gel in FIG. 6 shows that exon 1 does not generate a detectable SNP product band. To increase the signal of exon 1, blocking sequences of 8, 10, and 12 nucleotides were inserted into the biotinylated forward primers of exon 1 of the cytochrome P450 CYP2D6 gene as set forth below; the fourth exon 1 primer represents the reverse primer.

```
Exon1B8PR1
5'-~CCA CCA GC X T AGT GGC CAT CTT CCT GCT C    (SEQ ID NOS: 9-
                                                10)

Exon1B10PR1
5'-~GT CCA CCA GC X T AGT GGC CAT CTT CCT GCT C  (SEQ ID NOS: 11-
                                                12)

Exon1B12PR1
5'-~A GGT CCA CCA GC X T AGT GGC CAT CTT CCT GCT C (SEQ ID NOS: 13-
                                                14)

Exon1PR2
5'-~TCT GGT AGG GGA GCC TCA G                  (SEQ ID NO: 15)
   X: ethyleneglycol spacer 18
```

Figure 7:
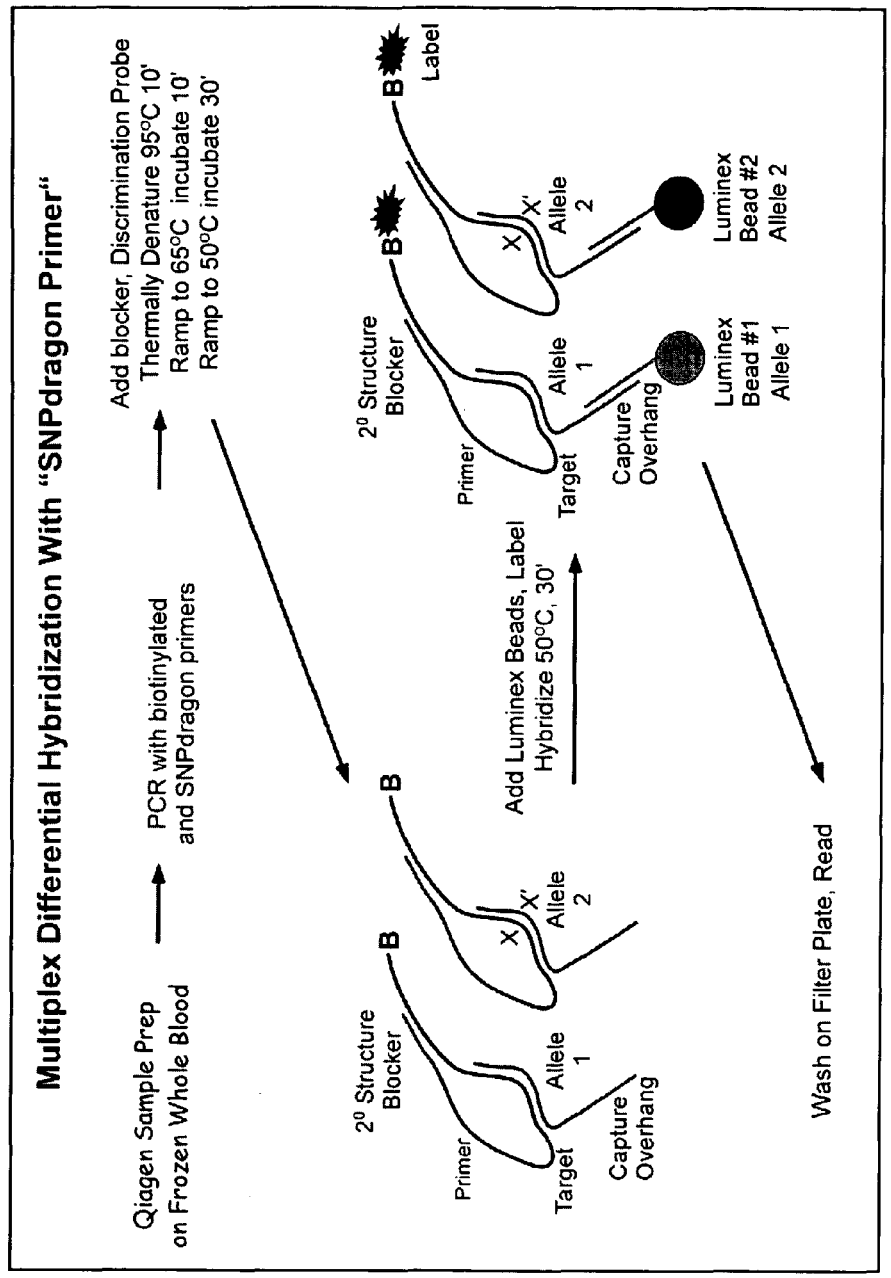
FIG. 7 schematically illustrates multiplex differential hybridization with the dual-purpose primers of the invention.
Figure 8:
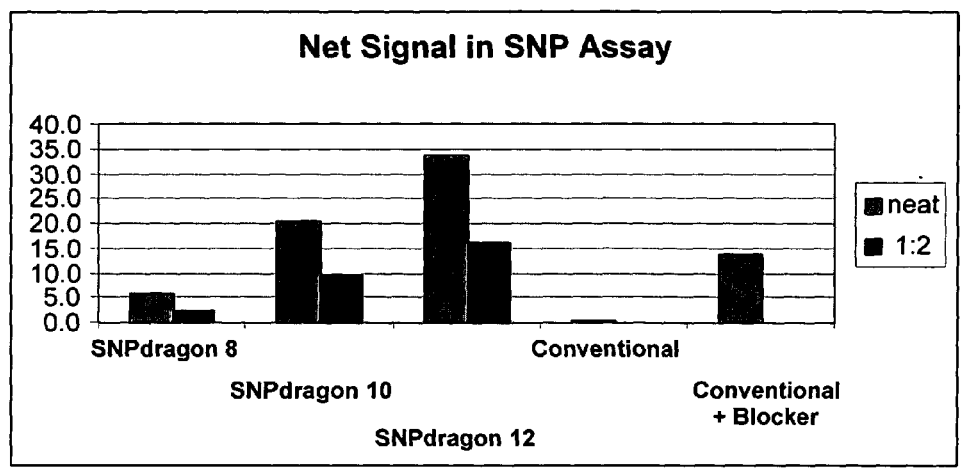
FIG. 8 is a bar graph comparing the results of the multiplex PCR assay used to detect SNPs in exon 1 of the cytochrome P450 CYP2D2 gene (SNP assay) using dual-purpose primers of the invention having 8, 10, or 12 nucleotide inserts, conventional primers, and conventional primers used in combination with a blocking oligonucleotide.

Disruption of Secondary Structure:

To determine the effectiveness of the dual-purpose primer molecules at disrupting the secondary structure formed within the cytochrome P450 CPY2D2 exon 1 PCR amplicon, 1 pmol/25 μL of individual dual-purpose primer molecules having blocking sequences of 8, 10, and 12 nucleotides, as set forth above, were added to the multiplex working reagent. Control blocker molecules were added at the same concentration. The cytochrome P450 SNP assay as set forth above was then performed using the dual-purpose primers. FIG. 7 is a schematic representation of this protocol. As shown in FIG. 8, the net signal detected in the SNP assay increased with the increasing length of the blocking sequences. By contrast, when no blocker sequence was used, little signal was generated (see column labeled "conventional" in FIG. 8). When a 25 nucleotide external blocker sequence was used with the conventional primer, a 15 to 20-fold increase in the signal was seen over the primer having no blocker (see column labeled "conventional+blocker" in FIG. 8); however, the effectiveness of the 25 nucleotide external blocker was significantly less than the effectiveness of the dual-purpose primer with the 12 nucleotide blocker insert; the latter showing a two-fold net increase in signal over the 25 nucleotide external blocker.

Example 2

Detection of Wild Type or Mutant Alleles for Exons 1, 2, 6, and 9 of Cytochrome P450 CPY2D6

To detect wild type or mutant alleles for exons 1, 2, 6, and 9 of the cytochrome P450 CPY2D6 gene, the multiplex PCR assay set forth above was used to detect SNPs in each of the four exons. To carry out this procedure, primer sets were designed to amplify the specific regions corresponding to exons 1, 2, 6, and 9 of the cytochrome P450 CYP2D6 gene. The resulting amplicons were hybridized via direct capture to ASH probes specific for the wild-type and mutant alleles. Where appropriate, dual purpose primers were used to disrupt secondary structure. Each of the ASH probes contained unique sequence domains complementary to a target sequence on a specific color-coded Luminex™ microsphere. To lower potential cross-reactivity between capture sequences on the ASH probes and the Luminex™ microspheres, non-natural iso-cytosine and iso-guanine bases were incorporated into the capture sequences on the ASH probes and the Luminex™ microspheres. Using this multiplexing assay, the mutant and wild-type alleles were readily identifiable according to the color of the Luminex™ microspheres.

The ASH probes and Tm for each of the wild-type (top) and mutant (bottom) alleles of exons 1, 2, 6, and 9 of the cytochrome P450 CPY2D6 gene are set forth below. The Tm for the ASH probes designed to hybridize with the wild-type amplicon sequences are at least 10° C. more stable (i.e., melting at least 10° C. higher) than the ASH probes designed to hybridize with mutant amplicon sequences. These melting temperatures are consistent with the 10° C. predicted difference in melting temperatures for one base pair mismatched sequences. Under this rubric, the allele specific hybridization probe for mutant amplicon sequences will be more stable by at least 10° C. when the mutant amplicon sequences are present.

```
Exon 1 C
5'-JTATJCGCJCTGFTATJCCG CCTGGTGGGTAGC FGGCJFCTJGACJATFFTATCT      (SEQ ID NO: 16)
        Tm = 47.7° C.

Exon 1 T
5'-JTATJCGCJCTGFTATJCCG CCTGGTGAGTAGC FAAGJTGGFAAJJAFCJTGCCT      (SEQ ID NO: 17)
        Tm = 36.3° C.

Exon 2 C
5'-JTATJCGCJCTGFTATJCCG ATCTGGGTGATGGG JAGGFACJTCJGATGFATFGCT    (SEQ ID NO: 18)
        Tm = 47.9° C.

Exon 2 T
5'-JTATJCGCJCTGFTATJCCG ATCTGGATGATGGG JATFGGFAACGFACFCTJGTGT    (SEQ ID NO: 19)
        Tm = 37.2° C.

Exon 6 C
5'-JTATJCGCJCTGFTATJCCG CTATGCGCAGGTTC TGCAFGFTGJAFAGAJCCAAFGT   (SEQ ID NO: 20)
        Tm = 48.4° C.

Exon 6 T
5'-JTATJCGCJCTGFTATJCCG CTATGCACAGGTTC GAJGATFCAFGGAJCCFTTJGAGTT (SEQ ID NO: 21)
        Tm = 38.7° C.

Exon 9 G
5'-JTATJCGCJCTGFTATJCCG GATGGGCTCACCA AJCACTFGAJTGFGATJTAFCGJT   (SEQ ID NO: 22)
        Tm = 46.9° C.

Exon 9 C
5'-JTATJCGCJCTGFTATJCCG GATGGGGTCACCA CGGCFACJCTCTFAGFGAAJTGTT   (SEQ ID NO: 23)
        Tm = 26.5° C.
Where J = iso-guanine, and F = iso-cytosine.
```

Figure 9:
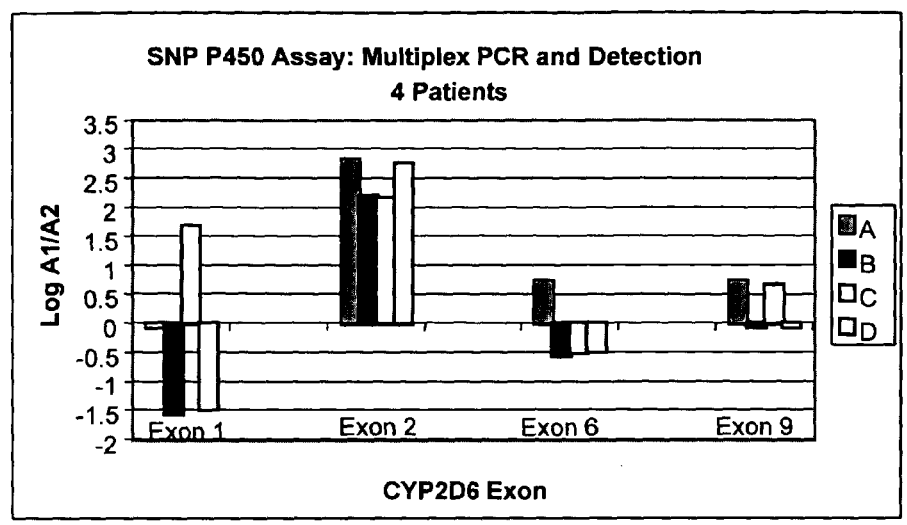
FIG. 9 is a bar graph demonstrating the cytochrome P450 genotyping results of a multiplex SNP assay conducted on four individual patient samples.

FIG. 2 shows a schematic representation of the multiplex PCR assay and the capture of the of the wild-type and mutant alleles to their respective Luminex™ microspheres; FIG. 7 schematically shows the interplay of the dual-purpose primer in the SNP assay; and FIG. 9 shows the results of the multiplex PCR assay to detect the genotype of exons 1, 2, 6, and 9 of the cytochrome P450 CYP2D2 gene for four individual patients.

We claim:

1. A dual-purpose primer for amplifying a target nucleotide sequence in a target molecule, wherein the target molecule has a secondary structure forming region and further wherein the target nucleotide sequence contains a site of interest proximal to or contained within the secondary structure forming region wherein the primer comprises: (a) a primer sequence complementary to a segment of the target nucleotide sequence other than the secondary structure forming region; and (b) a blocking sequence substantially complementary to a segment of the secondary structure forming region, wherein the blocking sequence disrupts formation of the unwanted secondary structure in an amplicon thereby enabling detection and amplification of the site of interest.

2. The primer of claim 1, wherein the site of interest is a nucleic acid sequence.

3. The primer of claim 2, wherein the site of interest is a single nucleotide polymorphism.

4. The primer of claim 1, wherein the primer sequence is complementary to one terminus of the target molecule containing the target nucleotide sequence.

5. The primer of claim 1, further including a nonhybridizing spacer between the primer sequence and the blocking sequence.

6. The primer of claim 5, wherein the spacer is non-nucleotidic.

7. The primer of claim 6, wherein the spacer is comprised of a synthetic hydrophilic oligomer.

8. The primer of claim 7, wherein the spacer is comprised of about 3 to about 50 alkylene oxide units selected from ethylene oxide and combinations of ethylene oxide and propylene oxide.

9. The primer of claim 5, wherein the spacer is nucleotidic.

10. The primer of claim 9, wherein the spacer is comprised of a sequence of non-natural nucleotides.

11. The primer of claim 10, wherein the non-natural nucleotides are selected from iso-guanine and iso-cytosine.

12. The primer of claim 9, wherein the spacer is an oligomeric segment of a recurring single nucleotide.

13. The primer of claim 9, wherein the probe primer sequence and the spacer are separated from each other by a means for halting transcription therebetween.

14. The primer of claim 13, wherein the means for halting transcription is an arresting linker.

15. The primer of claim 14, wherein the arresting linker comprises at least one modified nucleoside.

16. The primer of claim 15, wherein the modified nucleoside is an $N^4$-modified pyrimidine.

17. The primer of claim 1, further comprising a detectable label.

18. The primer of claim 17, wherein the detectable label is selected from the group consisting of fluorescers, chemiluminescers, dyes, biotin, haptens, enzymes, enzyme substrates, enzyme cofactors, enzyme inhibitors, enzyme subunits, metal ions, electron-dense reagents, and radioactive isotopes.

19. An amplicon formed by the action of a DNA polymerase on the primer of claim 1 hybridized to the target nucleotide sequence.

20. A kit for determining the genotype of an individual, comprising a dual-purpose primer according to claim 1, nucleotides appropriate to amplification of an oligonucleotide sequence, and an agent for polymerization of the nucleotides.

21. A kit for determining the genotype of an individual, comprising a dual-purpose primer according to claim 1, a second primer, nucleotides appropriate to DNA amplification, an agent for polymerization of the nucleotides, an allele specific hybridization (ASH) probe having a nucleotide capture region, and color-coded detecting means having a nucleotide capture region complementary to the nucleotide capture region on said ASH probe, wherein the nucleotide capture region on said detecting means is complementary to said ASH probe such that the target nucleotide sequence is identified by the color-coding of said detecting means.

22. The kit of claim 21, wherein the detecting means is a multiplex detecting means.

23. The kit of claim 22, wherein the multiplex detecting means comprises a detectable solid substrate.

24. The kit of claim 23, wherein the detectable solid substrate is a detectable microsphere.

25. A hybridization probe comprising (a) a probe nucleotide sequence complementary to a first nucleotide sequence in a target molecule, and (b) a blocking sequence substantially complementary to a second nucleotide sequence located within a secondary structure formation in the target molecule, wherein the secondary structure formation interferes with hybridization of the probe nucleotide sequence to the first nucleotide sequence and further wherein hybridization of the blocking sequence with the second nucleotide sequence disrupts the secondary structure formation in the second nucleotide sequence such that the probe nucleotide sequence is able to hybridize to the first nucleotide sequence.

26. The hybridization probe of claim 25, further comprising a detectable label.

27. The hybridization probe of claim 26, wherein the detectable label is selected from the group consisting of chemiluminescent labels, fluorescent labels, radioactive labels, multimeric DNA labels, dyes, enzymes, enzyme modulators, detectable solid substrates, and metal ions.

* * * * *

UNITED STATES PATENT AND TRADEMARK OFFICE
CERTIFICATE OF CORRECTION

PATENT NO.        : 8,394,944 B2                                      Page 1 of 1
APPLICATION NO.   : 10/667191
DATED             : March 12, 2013
INVENTOR(S)       : Zheng et al.

It is certified that error appears in the above-identified patent and that said Letters Patent is hereby corrected as shown below:

In the Claims:

Column 32, line 50 through 52, delete claim 13 and substitute the following:

13. The primer of claim 9, wherein the primer sequence and the spacer are separated from each other by a means for halting transcription therebetween.

Signed and Sealed this
Fourth Day of June, 2013

Teresa Stanek Rea
*Acting Director of the United States Patent and Trademark Office*

SEQUENCE LISTING

```
<160> NUMBER OF SEQ ID NOS: 28

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 1
tagtggccat cttcctgctc                                                20

<210> SEQ ID NO 2
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 2
tctggtaggg gagcctcag                                                 19

<210> SEQ ID NO 3
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 3
cttcggggac gtgttcag                                                  18

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 4
tcccacggaa atctgtctct                                                20

<210> SEQ ID NO 5
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 5
cccgttctgt cccgagtat                                                 19

<210> SEQ ID NO 6
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 6
```

-continued

| | |
|---|---|
| gtttcccaga tgggctcac | 19 |

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Primer
<400> SEQUENCE: 7

| | |
|---|---|
| ccatggtgtc tttgctttcc | 20 |

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Primer
<400> SEQUENCE: 8

| | |
|---|---|
| gtggggtaag caggaatgag | 20 |

<210> SEQ ID NO 9
<211> LENGTH: 8
<212> TYPE: DNA
<213> ORGANISM: Artificial Sequence
<220> FEATURE:
<223> OTHER INFORMATION: Description of Artificial Sequence: Primer
<400> SEQUENCE: 9

| | |
|---|---|
| ccaccagc | 8 |

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Primer
<400> SEQUENCE: 10

| | |
|---|---|
| tagtggccat cttcctgctc | 20 |

<210> SEQ ID NO 11
<211> LENGTH: 10
<212> TYPE: DNA
<213> ORGANISM: Artificial Sequence
<220> FEATURE:
<223> OTHER INFORMATION: Description of Artificial Sequence: Primer
<400> SEQUENCE: 11

| | |
|---|---|
| gtccaccagc | 10 |

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Primer
<400> SEQUENCE: 12

| | |
|---|---|
| tagtggccat cttcctgctc | 20 |

<210> SEQ ID NO 13
<211> LENGTH: 12
<212> TYPE: DNA
<213> ORGANISM: Artificial Sequence
<220> FEATURE:

-continued

<223> OTHER INFORMATION: Description of Artificial Sequence: Primer

<400> SEQUENCE: 13
aggtccacca gc                                                        12

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 14
tagtggccat cttcctgctc                                                20

<210> SEQ ID NO 15
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 15
tctggtaggg gagcctcag                                                 19

<210> SEQ ID NO 16
<211> LENGTH: 55
<212> TYPE: DNA
<213> ORGANISM: Artificial Sequence
<220> FEATURE:
<223> OTHER INFORMATION: Description of Artificial Sequence: Probe

<400> SEQUENCE: 16
gtatgcgcgc tgctatgccg cctggtgggt agccggcgcc tggacgatcc tatct         55

<210> SEQ ID NO 17
<211> LENGTH: 55
<212> TYPE: DNA
<213> ORGANISM: Artificial Sequence
<220> FEATURE:
<223> OTHER INFORMATION: Description of Artificial Sequence: Probe

<400> SEQUENCE: 17
gtatgcgcgc tgctatgccg cctggtgagt agccaaggtg gcaaggaccg tgcct         55

<210> SEQ ID NO 18
<211> LENGTH: 56
<212> TYPE: DNA
<213> ORGANISM: Artificial Sequence
<220> FEATURE:
<223> OTHER INFORMATION: Description of Artificial Sequence: Probe

<400> SEQUENCE: 18
gtatgcgcgc tgctatgccg atctgggtga tggggaggca cgtcggatgc atcgct        56

<210> SEQ ID NO 19
<211> LENGTH: 56
<212> TYPE: DNA
<213> ORGANISM: Artificial Sequence
<220> FEATURE:
<223> OTHER INFORMATION: Description of Artificial Sequence: Probe

<400> SEQUENCE: 19
gtatgcgcgc tgctatgccg atctggatga tggggatcgg caacgcaccc tggtgt        56

<210> SEQ ID NO 20

```
<211> LENGTH: 57
<212> TYPE: DNA
<213> ORGANISM: Artificial Sequence
<220> FEATURE:
<223> OTHER INFORMATION: Description of Artificial Sequence: Probe

<400> SEQUENCE: 20
gtatgcgcgc tgctatgccg ctatgcgcag gttctgcacg ctggacagag ccaacgt      57

<210> SEQ ID NO 21
<211> LENGTH: 59
<212> TYPE: DNA
<213> ORGANISM: Artificial Sequence
<220> FEATURE:
<223> OTHER INFORMATION: Description of Artificial Sequence: Probe

<400> SEQUENCE: 21
gtatgcgcgc tgctatgccg ctatgcacag gttcgaggat ccacggagcc cttggagtt    59

<210> SEQ ID NO 22
<211> LENGTH: 57
<212> TYPE: DNA
<213> ORGANISM: Artificial Sequence
<220> FEATURE:
<223> OTHER INFORMATION: Description of Artificial Sequence: Probe

<400> SEQUENCE: 22
gtatgcgcgc tgctatgccg gatgggctca ccaagcactc gagtgcgatg taccggt      57

<210> SEQ ID NO 23
<211> LENGTH: 57
<212> TYPE: DNA
<213> ORGANISM: Artificial Sequence
<220> FEATURE:
<223> OTHER INFORMATION: Description of Artificial Sequence: Probe

<400> SEQUENCE: 23
gtatgcgcgc tgctatgccg gatggggtca ccacggccac gctctcagcg aagtgtt      57

<210> SEQ ID NO 24
<211> LENGTH: 268
<212> TYPE: DNA
<213> ORGANISM: Homo sapiens

<400> SEQUENCE: 24
gctgagagtg tcctgcctgg tcctctgtgc ctggtggggt gggggtgcca ggtgtgtcca    60
gaggagccca tttggtagtg aggcaggtat ggggctagaa gcactggtgc ccctggccgt   120
gatagtggcc atcttcctgc tcctggtgga cctgatgcac cggcgccaac gctgggctgc   180
acgctaccca ccaggccccc tgccactgcc cgggctgggc aacctgctgc atgtggactt   240
ccagaacaca ccatactgct tcgaccag                                      268

<210> SEQ ID NO 25
<211> LENGTH: 172
<212> TYPE: DNA
<213> ORGANISM: Homo sapiens

<400> SEQUENCE: 25
ttgcggcgcc gcttcgggga cgtgttcagc ctgcagctgg cctggacgcc ggtggtcgtg    60
ctcaatgggc tggcggccgt gcgcgaggcg ctggtgaccc acggcgagga caccgccgac   120
cgcccgcctg tgcccatcac ccagatcctg ggtttcgggc gcgttcccaa ag           172

<210> SEQ ID NO 26
```

```
<211> LENGTH: 142
<212> TYPE: DNA
<213> ORGANISM: Homo sapiens

<400> SEQUENCE: 26
gccaagggga accctgagag cagcttcaat gatgagaacc tgcgcatagt ggtggctgac      60
ctgttctctg ccgggatggt gaccacctcg accacgctgg cctggggcct cctgctcatg     120
atcctacatc cggatgtgca gc                                              142

<210> SEQ ID NO 27
<211> LENGTH: 252
<212> TYPE: DNA
<213> ORGANISM: Homo sapiens

<400> SEQUENCE: 27
gccgccgtgc atgcctcggg gagcccctgg cccgcatgga gctcttcctc ttcttcacct      60
ccctgctgca gcacttcagc ttctcggtgc ccactggaca gccccggccc agccaccatg     120
gtgtctttgc tttcctggtg agcccatccc cctatgagct ttgtgctgtg ccccgctaga    180
atggggtacc tagtccccag cctgctccct agccagaggc tctaatgtac aataaagcaa    240
tgtggtagtt cc                                                         252

<210> SEQ ID NO 28
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
cggtgcatca ggtccaccag g                                                21
```